United States Patent [19]

Kondo et al.

[11] Patent Number: 5,614,520
[45] Date of Patent: Mar. 25, 1997

[54] 2-ARYLTHIAZOLE DERIVATIVES AND PHARMACEUTICAL COMPOSITION THEREOF

[75] Inventors: Shiro Kondo, Hachioji; Hisashi Fukushima, Hino; Masaichi Hasegawa, Hino; Masahiro Tsuchimoto, Hino; Ikuo Nagata, Hino; Yoshio Osada, Hino; Keiji Komoriya, Hachioji; Hisao Yamaguchi, Hino, all of Japan

[73] Assignee: Teijin Limited, Osaka, Japan

[21] Appl. No.: 380,214

[22] Filed: Jan. 30, 1995

Related U.S. Application Data

[63] Continuation of Ser. No. 917,037, filed as PCT/JP91/01670, Nov. 29, 1991, abandoned.

[30] Foreign Application Priority Data

Nov. 30, 1990 [JP] Japan ..................... 2-330147
Aug. 2, 1991 [JP] Japan ..................... 3-216586

[51] Int. Cl.[6] ............... C07D 277/56; C07D 277/22; C07D 277/24; A61K 31/425
[52] U.S. Cl. ............... 514/236.8; 514/252; 514/326; 514/342; 514/365; 544/133; 544/367; 546/209; 546/270.4; 546/269.7; 548/188; 548/200; 548/201
[58] Field of Search ................. 514/365, 236, 514/8, 252, 326, 342, 4; 548/188, 200, 201; 544/133, 367; 546/209, 280

[56] References Cited

U.S. PATENT DOCUMENTS

| | | | |
|---|---|---|---|
| 3,852,293 | 12/1974 | Ariyan et al. | 546/280 |
| 4,020,080 | 4/1977 | Irick, Jr. et al. | 548/143 |
| 4,260,765 | 4/1981 | Harrison et al. | 546/280 |
| 4,363,813 | 12/1982 | Kawasaki et al. | 548/201 |
| 4,457,936 | 7/1984 | Draeger et al. | 548/201 |
| 4,528,291 | 7/1985 | Witkowski et al. | 546/280 X |
| 4,558,059 | 12/1985 | Kawasaki et al. | 548/200 |
| 4,571,402 | 2/1986 | Sunday et al. | 546/280 X |
| 5,124,342 | 6/1992 | Kerdesky et al. | 546/280 X |
| 5,244,867 | 9/1993 | Ditrich et al. | 548/201 X |

FOREIGN PATENT DOCUMENTS

| | | |
|---|---|---|
| 0033151 | 8/1981 | European Pat. Off. . |
| 2125251 | 11/1972 | Germany . |
| 2125193 | 11/1972 | Germany . |
| 3026054 | 2/1981 | Germany . |
| 3141430 | 5/1983 | Germany . |
| 59-16889 | 1/1984 | Japan . |
| 62-178590 | 8/1987 | Japan . |
| 63-112572 | 9/1988 | Japan . |
| 63-112574 | 9/1988 | Japan . |
| 2-229190 | 9/1990 | Japan . |
| 2084573 | 4/1982 | United Kingdom ............ 548/201 |
| 9009381 | 8/1990 | WIPO . |
| 9009801 | 9/1990 | WIPO . |

OTHER PUBLICATIONS

Chauvin et al, Chemical Abstracts, 82:125314e (1975).
Pons et al, Chemical Abstracts, 71:81350e (1969).
Robba et al, Chemical Abstracts, 66:94981h (1967).
Lechat et al., Chemical Abstracts, 75:10827e (1971).

*Primary Examiner*—Fiona T. Powers
*Attorney, Agent, or Firm*—Burgess, Ryan and Wayne

[57] ABSTRACT

Pharmaceutical compositions for treating gout or hyperuricemia and containing a new categorized compound, i.e. 2-arylthiazole derivatives, as an active ingredient, are provided. The 2-arylthiazole derivatives in the present invention are represented by the following formula (I):

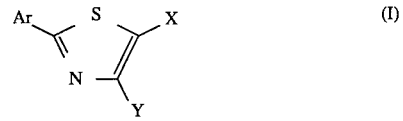

(I)

wherein
  Ar is an unsubstituted or substituted pyridyl, thienyl, furyl, naphthyl or phenyl group;
  X is a hydrogen atom, alkyl group or carboxyl group which may be protected, and
  Y is a hydrogen atom, alkyl group, or a hydroxyl or carbonyl group which may be protected.

Furthermore, novel compounds included in the 2-arylthiazole derivatives and pharmaceutically acceptable salts thereof are provided.

15 Claims, No Drawings

2-ARYLTHIAZOLE DERIVATIVES AND PHARMACEUTICAL COMPOSITION THEREOF

This application is a continuation of application Ser. No. 07/917,037, filed as PCT/JP91/01670, Nov. 29, 1991 now abandoned.

SPECIFICATION

1. Technical Field

The present invention relates to 2-arylthiazole derivatives or their pharmaceutically acceptable salts, and pharmaceutical compositions containing the same, and in particular, to the use thereof for treating gout or hyperuricemia, or diseases associated with a production of interleukin 1.

2. Background Art

It is recognized that human beings among animals, especially adult men, suffer from gout derived from hyperuricemia, including a lesion of renal stroma, blood vessels, urinary caculus, acute arthritis and gouty tophus caused by lithogenesis.

In the treatment of the gout, colchicine or a non-steroidal anti-inflammatory drug is used during the acute arthritic attack, and an hypouricemic therapy for hyperuricemia is conducted after a remission of the attack. The therapeutic agent for hyperuricemia is roughly classified into a uricosuric accelerator and a uricopiesis inhibitor, which can be properly selected depending upon the conditions and severity of diseases. Examples of the former include probenecid and benzbromarone. Allopurinol, which is a structural isomer of hypoxanthine, has long been used as the latter. Allopurinol inhibits xanthine oxidase and prevents the formation of uric acid from hypoxanthine and xanthine, to thus lower the serum uric acid level. Although the enzyme inhibitors of this type have been widely studied, using xanthine derivatives in the main, no drug has yet been found to safety requirements, and only allopurinol is applied to alleviate gout. Japanese Unexamined Patent Publication (Kokai) Nos. 57-85379 and 59-95272 disclose that isothiazole and a pyrazole derivatives inhibit xanthine oxidase to lower the serum uric acid level in mammal, but to date, none are in use for clinical applications.

On the other hand, a variety of 2-arylthiazole derivatives, and their synthetic intermediates has been proposed to have various physiological activities such as anti-inflammatory, analgesic, antimicrobial and antitumor activities, and inhibitory activity for prolyle or lysylehydroxylase. Also, it is known that 2-arylthiazole derivatives are used in the dye art. Among the known compounds, 2-arylthiazole derivatives having a methylcarboxyl group (—CH$_2$COOH or its ester) at the 5- or 4-position of the thiazole ring have found to possess anti-inflammatory or analgesic action, the compounds are studied in the art (see, for example, Spanish Patent No. 499110, GB Patent No. 687981 or Japanese Examined Patent Publication (Kokoku) No. 43-19307, GB Patent No. 1137529 or Japanese Examined Patent Publication (Kokoku) No. 47-41353, GB Patent No. 1145884 or Japanese Examined Patent Publication (Kokoku) No. 49-38267, DE-A-1917432 or Japanese Examined Patent Publication (Kokoku) No. 47-7368, GB Patent No. 1574583, BE Patent No. 888252). In synthetic intermediates or final products of the other physiologically active substances or dyes, there are included 2-arylthiazole derivatives having a carboxyl group, or either an ester or amide group derived from same at a 4- or 5- position in a thiazole ring thereof, for example, A. Benko et al., *Chem. Ber.* 100, (1967) 7, 2184–87, discloses 4-methyl-2-phenyl-5-thiazolecarboxylic acid and m-nitro or p-nitro substituted compounds on a phenyl group thereof; DE-A-3026054 or Japanese Examined Patent Publication (Kokoku) No. 63-10701, and Japanese Examined Patent Publication (Kokoku) No. 63-10950 disclose 2-phenyl-5-thiazolecarboxylic acid derivatives in which the 2-phenyl moiety has three methoxy groups for antiulcer; DE-A-1959307 discloses a variety of dyes prepared from 2-phenyl-5-thiazole carboxylic acid as a starting material; DE-A-3141430, DE-A-2125193 and DE-A-2125251 disclose 2-phenyl-5-thiazolecarboxylic acid derivatives in which the 2-phenyl moiety is tri-substituted by nitro, amino and azo groups, as used for dye and synthetic intermediates thereof; U.S. Pat. No. 3,518,279 discloses, as used for synthetic intermediates of an insecticide, 2-phenyl-5-thiazolecarboxylic acid derivatives in which the 2-phenyl moiety has substituent(s) such as a halogen atom, loweralkyl, alkoxyl, alkylamino or acylamino group, and further, has a carboxylic ester residue at a 5-position of same; and DE-C-3002989 discloses 2-phenyl-4-thiazole-carboxylic acid derivatives in which the 2phenyl moiety has a hydroxyl group at a 2'-position, a hydrogen atom, methyl group, halogen atom, nitro group, amino group or sulfonamide group at a 3'- or 5'-position, and a hydrogen atom, hydroxyl or methyl group at a 4'-position of same, as an inhibitor of prolyle- or lysyle-hydroxylase.

Furthermore, in a synthetic investigation of thiazole derivatives, 2-aryl-5-thiazolecarboxylic acid derivatives are disclosed as intermediates (for example, *Arch. Pharm.* (Weinheim) 309 (1976) 2, 128–130).

Nevertheless, in the prior art, it is neither described nor suggested that each disclosed 2-arylthiazole derivative has a xanthine oxidase inhibitory activity or uric acid-decreasing activity, or an inhibitory activity to production of interleukin 1 or arthritis associated with a production of same.

DISCLOSURE OF THE INVENTION

The present inventors have conducted extensive and intensive research into the provision of a useful compound for a xanthine oxidase inhibitor, from a different viewpoint to that of prior investigations into the inhibitor, and as a result, have accomplished the present invention based upon a finding that some 2-arylthiazole derivatives have a high xanthine oxidase inhibitory activity or uric acid decreasing action, and thus are efficacious against gout or hyperuricemia, and further, have a high inhibitory activity against the production of interleukin 1.

Therefore, in accordance with the present invention, pharmaceutical compositions comprising an effective amount of a 2-arylthiazole derivative having the following formula (I) or pharmaceutically acceptable salt thereof for treating diseases selected from a group consisting of gout or hyperuricemia and diseases associated with a production of interleukin 1, are provided:

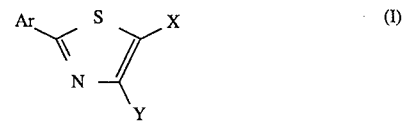

wherein

Ar represents an unsubstituted or substituted pyridyl, thienyl, furyl or naphthyl group, or a group having the following formula (II)

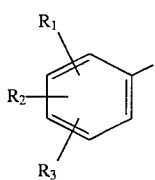

(II)

wherein $R_1$, $R_2$ and $R_3$, independently of each other, represent a hydrogen or halogen atom, or a nitro, cyano, formyl, $C_{1-4}$ alkyl or $C_{1-4}$ haloalkyl group, or a group of OR, $S(O)_nR$ and NRR' (wherein n is an integer from 0 to 2, R and R' is independently a hydrogen atom, or an unsubstituted or substituted $C_{1-10}$ alkyl, aryl, aralkyl, alkylcarbonyl, arylcarbonyl or aralkylcarbonyl group; or R and R', taken together with the nitrogen atom bonded thereof, represent atoms to form an unsubstituted or substituted 5- to 7- membered heterocyclic ring); or a group of COR" (wherein R" is an unsubstituted or substituted $C_{1-10}$ alkyl, aryl or aralkyl group; a hydroxyl group; an unsubstituted or substituted $C_{1-10}$ alkoxy, aryloxy or aralkyloxy group; an amino group; an unsubstituted or substituted $C_{1-0}$ alkyl (mono- or di-substituted, independently) amino, aryl (mono- or di-substituted, independently) amino or aralkyl (mono- or di-substituted, independently) amino group, or a 5- to 7membered cyclic amino group);

X represents a hydrogen atom, or a $C_{1-4}$ alkyl, carboxyl, $C_{1-5}$ alkoxycarbonyl, carbamoyl or $C_{1-4}$ alkyl (mono- or di-substituted)aminocarbonyl group; and Y represents a hydrogen atom, or a $C_{1-4}$ alkyl, hydroxyl, $C_{1-4}$ alkoxy, carbamoyl, $C_{1-5}$ alkoxycarbonyl, carboxylic amide or $C_{1-4}$ alkyl (mono- or di-substituted) aminocarbonyl group.

Furthermore, in accordance with the present invention, novel compounds within the 2-arylthiazole derivatives having the formula (I) are provided.

BEST MODE OF CARRYING OUT THE INVENTION

Each group of the 2-arylthiazole derivative according to the present invention is particularly disclosed below.

Ar is an unsubstituted or substituted pyridyl, thienyl, furyl or naphthyl group; or a group represented by the following formula (II)

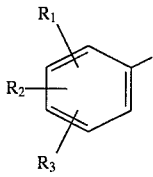

wherein $R_1$, $R_2$ and $R_3$ are as defined above.

According to the above-described definition, substituents which may have further substituent(s), i.e., pyridyl, thienyl, furyl or naphthyl group; $C_{1-10}$ alkyl, aryl, aralkyl, alkylcarbonyl, arylcarbonyl or aralkylcarbonyl group; 5- to 7- membered heterocyclic ring; $C_{1-10}$ alkoxy, aryloxy or aralkyloxy group; and $C_{1-10}$ alkyl (mono- or di-substituted) amino, aryl (mono- or disubstituted) amino group, on chain or cyclic moiety thereof, are substituted by one or more $C_{1-4}$ alkyl, halogenated alkyl, carboxyl, alkylcarbonyl, alkyloxy, alkylcarbonyloxy, hydroxyl, mono- or di-substituted alkylamino, amino, nitro, cyano or formyl group, or halogen atom (e.g., fluorine, chlorine, bromine, iodine), heterocyclic ring such as 5- to 7- membered cyclic-secondary amino group, etc. Preferred groups of such substituents are a halogen atom, methyl group, ethyl group, methoxy group and ethoxy group.

Examples of the halogen atom include fluorine, chlorine, bromine and iodine atoms, as described above, and chlorine and fluorine are preferred. Examples of the $C_{1-4}$ alkyl group include methyl group, ethyl group, (iso- or n-)propyl group and (iso-, n-, tert- or sec-)butyl group, and a methyl group and a tert-butyl group are preferred. Examples of the $C_{1-4}$ haloalkyl group include a haloalkyl group comprising the above-described halogen atom and alkyl group, and a trifluoromethyl group is preferred.

In the present invention, the term "$C_{1-10}$ alkyl group" as R, R' and R" is intended to mean a $C_{1-10}$ straight-chain or branched aliphatic hydrocarbon residue, cyclic aliphatic hydrocarbon residue or chain-cyclic aliphatic hydrocarbon residue, and examples thereof include methyl, ethyl, n-propyl, iso-propyl, n-butyl, iso-butyl, sec-butyl, tert-butyl, n-pentyl, iso-pentyl, neo-pentyl, n-hexyl, n-octyl, cyclopropyl, cyclobutyl, cyclopentyl, cyclohexyl, cyclopropylmethyl, cyclohexylmethyl, cyclohexylpropyl, methoxyethyl, ethoxyethyl, and the like.

Examples of the aryl group include aromatic hydrocarbon residues or aromatic heterocyclic ring groups comprising 5- or 6-membered monocyclic or fused ring, for example, phenyl, 1-naphthyl, 2-naphthyl, 2-pyrrolyl, 2-furyl, 2-thienyl, 2-pyridyl, and the like.

The aralkyl group is a group comprising the above-described lower alkyl or aryl group having a number of constituent atoms of 6 to 10 and aryl group, and examples thereof include lower aralkyl groups such as benzyl, 1-phenylethyl, 1-methyl-1-phenylethyl, 2-phenylethyl, 3-phenylpropyl, cinnamyl, 2-pyrrolylmethyl, furfuryl, thenyl, and the like, and a benzyl group is preferred.

In the present invention, the alkylcarbonyl group is a group comprising the above-described lower alkyl group and a carbonyl group, and examples thereof include $C_{2-7}$ lower aliphatic acyl groups such as acetyl, propanoyl, butanoyl, 2-methylpropanoyl, pentanoyl, 2-methylbutanoyl, 3-methylbutanoyl, pivaloyl, hexanoyl, cyclopropylcarbonyl, and the like. The arlylcarbonyl group is a group comprising the above-described aryl group and a carbonyl group, and examples thereof include benzoyl, toluoyl, 2-pyrrolcarbonyl, 2-fluoyl, 2-thiophenecarbonyl, and the like. The aralkylcarbonyl group is a group comprising the above-described aralkyl group and a carbonyl group, and examples thereof include $C_{5-10}$ aralkylcarbonyl groups such as phenylacetyl, 3-phenylpropanoyl, 4-phenylbutanoyl, cinnamoyl, 2-pyrrolylacetyl, 2-furylacetyl, 2-thienylacetyl, and the like.

According to the above-described definition of R, examples of OR include ethoxy, (n- or iso-)propoxy, (n-, iso-, sec- or tert-)butoxy, pentyloxy, n-hexyloxy, cyclopropylmethyloxy, cyclohexyloxy, phenyloxy, benzyloxy, phenetyloxy, methoxethyloxy, ethoxyethyloxy, acetoxy, propanoyloxy, butanoyloxy, benzoyloxy, and the like.

According to the above-described definition of R, examples of the $S(O)_n$ R include ethylthio, isopropylthio, isopropylsulfinyl, isopropylsulfonyl, pentylsulfonyl, phenylthio, phenylsulfinyl, phenylsulfonyl, and the like.

According to the above-described definition of R and R', examples of the NRR' include dimethylamino, diethylamino, benzylamino, phenethylamino, and the like, and where R and R' taken together with each other nitrogen atom bonded thereof, represent atoms to form an unsubstituted or substituted 5- to 7-membered heterocyclic ring, examples of the heterocyclic ring include morpholino, 1-pyrrolyl, 1-pyrrolidinyl, piperidino, piperazino, and the like.

According to the above-described definition of R", when R" is a $C_{1-10}$ alkoxy group of the COR", R" is a group comprising the above-described alkyl group and an oxy group, and for example, includes methoxy, ethoxy, (n- or iso-)propoxy, (n-, iso-, sec- or tert-)butoxy, 3-methylbutoxy, 2-ethylbutoxy, pentyloxy, hexyloxy, 3-methyl-2-butenyloxy, geranyloxy, cyclopentyloxy, cyclohexyloxy, cyclohexyl-$C_{1-4}$-alkyloxy (e.g., cyclohexylmethyloxy), and the like.

The aryloxy group comprise the above-described aryl group and an oxy group, and examples thereof include phenoxy, 1-naphthoxy, and the like. The aralkyloxy group comprises the above-described aralkyl group and an oxy group, and for example, includes benzyloxy, 1-phenylethoxy, 1-methyl-1-phenylethoxy, and the like. The $C_{1-10}$ alkyl(mono- or di-substituted)amino group comprises the above-described alkyl group and an amino group, and examples thereof include methylamino, ethylamino, dimethylamino, diethylamino groups, and the like. The aryl-(mono- or di-substituted)amino group comprises the above-described aryl group and an amino group, and examples thereof include phenylamino, methylphenylamino, and the like. The aralkyl(mono- or di-substituted)amino group comprises the above-described aralkyl group and an amino group, and examples thereof include benzylamino, methylbenzylamino, and the like. Examples of the 5- to 7- membered cyclic-secondary amino group include morphorino, 1-pyrrolyl, 1-pyrrolidino, piperidino, and the like.

In the X and Y of the formula (I), the $C_{1-4}$ alkyl groups include methyl, ethyl, n-propyl, iso-propyl, n-butyl, iso-butyl, tert-butyl, and the like; the $C_{1-5}$ alkoxycarbonyl group is an alkoxycarbonyl in which the alkyl moiety has the above-described alkyl, and include, for example, methoxycarbonyl, ethoxycarbonyl, (n- or iso-) propoxycarbonyl or (n-, iso-, sec- or tert-)butoxy(or butyloxy)carbonyl; and the $C_{1-4}$ alkyl (mono- or di-substituted)aminocarbonyl group includes, for example, methylaminocarbonyl, ethylaminocarbonyl, dimethylaminocarbonyl, and the like.

The derivatives of the formula (I) used for the object of the invention, where the above-described substituent is a carboxyl group, can form a pharmaceutically acceptable salt together with non-toxic cations which will be described later, for example, sodium, potassium, and the like, or can be provided in the form of prodrug, and these salts and prodrugs can be used in the same manner as a free compound of the formula (I), respectively.

In accordance with the present invention, novel compounds within the above-described definition of 2-arylthiazole derivatives having the formula (I), which are not disclosed in known publications and in which each substituent is defined as described below, are provided. Namely, there are provided 2-arylthiazole derivatives having the formula (I):
wherein
Ar is an unsubstituted or substituted pyridyl, thienyl, furyl or naphthyl group; or a group represented by the following formula (II)

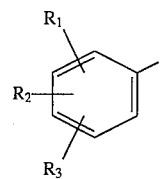

wherein
at least one group of $R_1$, $R_2$ and $R_3$ is a halogen atom, or a nitro, cyano, formyl or trifluoromethyl group; or a group of OR, $S(O)_nR$ and NRR' (wherein n is an integer from 0 to 2, R represents an unsubstituted or substituted $C_{1-10}$ alkyl, aryl, aralkyl, alkylcarbonyl, arylcarbonyl or aralkylcarbonyl group, R' represents a hydrogen atom, or an unsubstituted or substituted $C_{1-10}$ alkyl, aryl, aralkyl, alkylcarbonyl, arylcarbonyl or aralkylcarbonyl group; or R and R', taken together with the nitrogen atom bonded thereof, represent atoms forming an unsubstituted or substituted 5- to 7- membered heterocyclic ring), or a group of COR" (wherein R" represents and unsubstituted or substituted $C_{1-10}$ alkyl, aryl or aralkyl group; a hydroxyl group; an unsubstituted or substituted $C_{1-10}$ alkoxy, aryloxy or aralkyloxy group; an amino group; or an unsubstituted or substituted $C_{1-10}$ alkyl(mono- or di-substituted, independently)amino, aryl(mono- or di-substituted, independently)amino or aralkyl(mono- or di-substituted, independently)amino group, or a 5- to 7- membered cyclic amino group);

X represents a hydrogen atom, or a $C_{1-4}$ alkyl, carboxyl, $C_{1-5}$ alkoxycarbonyl, carbamoyl or $C_{1-4}$ alkyl (mono- or di-substituted)aminocarbonyl group; and Y represents a hydrogen atom, or a $C_{1-4}$ alkyl, hydroxyl, $C_{1-4}$ alkoxy, carboxyl, $C_{1-5}$ alkoxycarbonyl, carbamoyl or $C_{1-4}$ alkyl(mono- or di-substituted) aminocarbonyl group, with the proviso that when at least one group of $R_1$, $R_2$ and $R_3$ represents a halogen atom, or a alkoxy, alkyamino or nitro group, at least one group of other two groups represents a group other than hydrogen atom; when at least one group of $R_1$, $R_2$ and $R_3$ is a halogen atom and another group is a hydrogen atom, a remaining group is a group other than the halogen atom, or an alkoxy, alkylamino or acylamino group; and pharmaceutically acceptable salts thereof.

Of these compounds, it is preferably the 2-arylthiazole derivatives are of the formula (I), wherein
Ar is a group representing the formula (II), and $R_1$ is a halogen atom, or a nitro, cyano, formyl or trifluoromethyl group; $R_2$ is a trifluoromethyl, or a group of OR, $S(O)_nR$ or NRR' (wherein n is an integer from 0 to 2, R represents an unsubstituted or substituted $C_{1-10}$ alkyl, aryl, aralkyl, alkylcarbonyl, arylcarbonyl or aralkylcarbonyl group; R' represents a hydrogen atom, or an unsubstituted or substituted $C_{1-10}$ alkyl, aryl, aralkyl, alkylcarbonyl, arylcarbonyl or aralkylcarbonyl group; or R and R', taken together with the nitrogen atom bonded thereof, represents atoms to form an unsubstituted or substituted 5- to 7- membered heterocyclic ring); and $R_3$ represents a hydrogen atom or a halogen atom;

X represents a carboxyl, $C_{1-5}$ alkoxycarbonyl, carbamoyl of $C_{1-4}$ alkyl(mono- or disubstituted)aminocarbonyl group; and Y represents a hydrogen atom, or $C_{1-4}$ alkyl, hydroxyl, $C_{1-4}$ alkoxy or carboxyl group; and pharmaceutically acceptable salts thereof.

Particularly, it is preferred that the 2-arylthiazole derivatives are of the formula (I) wherein, Ar is a group representing the formula (II), and $R_1$ is a m-nitro group, $R_2$ is a group of OR, $S(O)_nR$ and NRR' (wherein n is an integer from 0 to 2, R represents an unsubstituted or substituted $C_{1-10}$ alkyl, aryl, aralkyl, alkylcarbonyl, arylcarbonyl or aralkylcarbonyl group, R' represents a hydrogen atom, or an unsubstituted or substituted $C_{1-10}$ alkyl, aryl, aralkyl, alkylcarbonyl, arylcarbonyl or aralkylcarbonyl group; or R and R', taken together with the nitrogen atom bonded thereof, represents atoms to form an unsubstituted or substituted 5- to 7- membered heterocyclic ring), and $R_3$ represents a hydrogen atom; or $R_1$ is a m-halogen atom, or a m-cyano or m-trifluoromethyl group, $R_2$ is a group of OR, $S(O)_nR$ and NRR' (wherein n is an integer from 0 to 2, R represents an unsubstituted or substituted $C_{1-10}$ alkyl, aryl, aralkyl, alkylcarbonyl, arylcarbonyl or aralkylcarbonyl, R' represents a hydrogen atom, or an unsubstituted or substituted $C_{1-10}$ alkyl, aryl, aralkyl, alkylcarbonyl, arylcarbonyl or aralkylcarbonyl group; or R and R', taken together with the nitrogen atom bonded thereof, represents atoms to form an unsubstituted or substituted 5- to 7- membered heterocyclic ring), and $R_3$ is a hydrogen or halogen atom; or $R_1$ is a group of COR" (wherein R" represents an unsubstituted or substituted $C_{1-10}$ alkyl, aryl or aralkyl group); X and Y are as defined above, respectively; and pharmaceutically acceptable salts thereof.

Of such derivatives, in particular, it is preferred that a 2-arylthiazole derivative is selected from a group consisting of compounds having the following formula (I-a):

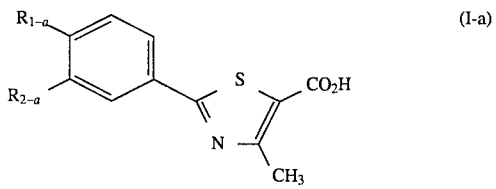

(I-a)

wherein $R_{1-a}$ is a $C_{2-8}$ alkoxy group, and $R_{2-a}$ is a nitro group;

$R_{1-a}$ is a $C_{2-8}$ alkoxy group, and $R_{2-a}$ is a trifluoromethyl group;

$R_{1-a}$ is a $C_{2-8}$ alkoxy group, and $R_{2-a}$ is a cyano group;

$R_{1-a}$ is a morpholino, 4-N-methyl-piperazine-1-yl or piperidino, and $R_{2-a}$ is a nitro, trifluoromethyl or cyano group; and $R_{1-a}$ is an unsubstituted or one or two of methyl, chloro or methoxy substituted benzoyl group, and $R_{2-a}$ is a hydrogen atom, and a pharmaceutically acceptable salt thereof.

Alternatively, it is preferred that a 2-arylthiazole derivative is selected from a group consisting of compounds having the following formula (I-b):

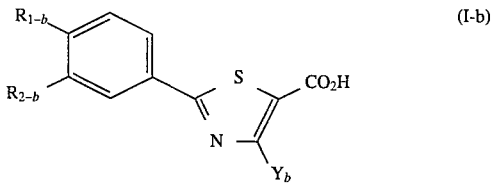

(I-b)

wherein $R_{1-b}$ is a group of OR and SR (wherein R is a $C_{2-8}$ alkyl group) or a morpholino, 4-N-methyl-piperazine-1-yl or piperidino, $R_{2-b}$ is a nitro, trifluoromethyl or cyano group, and $Y_b$ is a hydrogen atom or a methyl group; and $R_{1-b}$ is a group of the formula

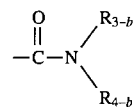

(wherein $R_{3-b}$ is an unsubstituted or substituted phenyl group, $R_{4-b}$ is a hydrogen atom, or a $C_{1-3}$ alkyl group, and $Y_b$ is a hydrogen atom or methyl group; and a pharmaceutically acceptable salt thereof.

Parts of the compounds hereinbefore set forth are well known in the art, and the novel compounds according to the present invention may be produced as a process of producing the known compound.

For example, the compounds can be generally prepare by known procedures as described in *Organic Reactions*, Vol. 6, 367–409(1951), or *Heterocyclic Compounds*, Vol. 34, (1978). Further, when Ar is represented by the formula (II), the compounds can be produced by the following process:

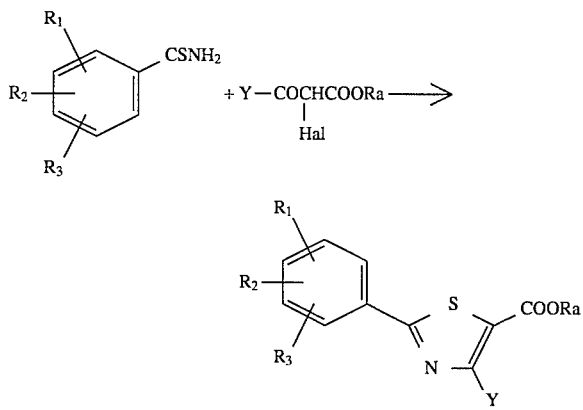

wherein $R_1$, $R_2$ and $R_3$ are as defined above in connection with the formula (II), Y is as defined above in connection with the formula (I), Hal represents a halogen atom, and $R_a$ represents a $C_{1-4}$ alkyl group.

Specifically, a substituted thiobenzamide and an alkyl ester of 2-halogeno-acylacetic acid are directly mixed or reacted with in solvent in the presence or absence of a base at a temperature in the range of room temperature to 200° C., preferably in the range of 50 to 100° C. Examples of the base include organic bases, such as triethylamine, pyridine and dimethylaminopyridine, and inorganic bases, such as anhydrous potassium carbonate and sodium hydroxide. The solvent may be any one as long as it has no adverse effect on the reaction, and examples thereof include hydrocarbons such as benzene, toluene and hexane, ethers such as dioxane and methylcellosolve, alcohols such as ethanol and isopropanol, and N,N-dimethylformamide, dimethylsulfoxide and acetonitrile. Among them, alcohols corresponding to the substituent Ra are preferred. The resultant ester derivative is hydrolyzed by a conventional process to provide a corresponding free acid.

The substituted thiobenzamide derivative is usually produced by adding phosphorus pentasulfide or a lawson reagent (see *Bull. Soc. Chim. Belg.* 87, 223 (1978)) from a corresponding benzamide in a solvent such as benzene.

It is also known that thiobenzamide is synthesized by adding hydrogen sulfide from a corresponding benzonitrile (see A. E. S. Fairfull et al., *J. Chem. Soc.*, 1952, 742). Note, the addition of thioacetamide in N,N-dimethylformamide saturated with hydrochloric acid followed by heating (see E. C. Taylor et al., *J. Am. Chem. Soc.*, 82, 2656 (1960)) is preferred from the viewpoint of yield, operating property and economy.

When a thiazole ring is formed, as described in *Organic Synthesis* III, 332 (1955) and Japanese Patent No. JP87055, an α-haloketone derivative may be allowed to react without isolation of a thioamide derivative or a thiobenzamide derivative.

When Ar is represented by a group other than the formula (II), an intended product can be produced in the same manner as that described above.

If necessary, the 2-aryl-5-thiazolecarboxylic acid derivative thus produced is converted to a salt thereof with a pharmaceutically acceptable non-toxic cation. Examples of this kind of cation include alkali metal cations such as Na and K, alkaline earth metal cations such as Mg and Ca, other metal cations used usually, such as Al and Zn and organic bases such as ammonia, triethylamine and pyridine. When the compounds represented by the formula (I) have an amino group in its molecule, they can be converted to corresponding acid addition salts. Examples of the acid include mineral acids such as hydrochloric acid, sulfuric acid and nitric acid and pharmaceutically acceptable organic acids such as acetic acid, benzoic acid, fumaric acid, maleic acid, methanesulfonic acid, toluenesulfonic acid or amino acids such as glycine and alanine.

The compounds produced in the present invention are provided in the form of oral preparations such as soft capsule, hard capsule, tablet, granule, powder, suspension, solution and syrup, injections, suppositories and external preparations by a conventional method through the use of a suitable excipient or the like. Examples of the excipient include vegetable oils (for example, corn oil, cotton seed oil, coconut oil, almond oil, peanut oil, olive oil, and the like), oily esters such as medium-length chain fatty acid glyceride oil, mineral oils, glycerin esters such as tricaprylin, triacetin, and the like, alcohols such as ethanol, and the like, physiological saline, propylene glycol, polyethylene glycol, petrolatum, animal fat and oil, cellulose derivatives (crystalline cellulose, hydroxypropyl cellulose, hydroxypropylmethyl cellulose, methyl cellulose), polyvinyl pyrrolidone, dextrin, lactose, mannitol, sorbitol, starch, and the like.

The dose of the active ingredient is usually about 1 to 500 mg/day/person, preferably 10 to 300 mg/day/person, and it is preferred for formulations to be conducted so as to satisfy such a requirement.

The present inventors have found that the 2-arylthiazole derivatives of the formula (I) have very high xanthine oxidase inhibitory activity and serum uric acid lowering activity against mammals and surprisingly have a strong interleukin 1 (IL-1) production inhibitory activity. IL-1 is known to induce the activation of leucocytes, the sthenia of production of an antibody, the sthenia of production of cytokine and $PGE_2$ from macrophage, the dissolution of bone, the fever, etc., and is considered to participate in chronic rheumatism, osteoarthritis, osteoporosis, tissue rejection, sepsis, toxicogenic shock syndrome, symptoms such as fever and respiratory diseases derived from infection of virus or bacteria (i.e., "influenza"), chronic nephritis, secondary cachexia derived from malignant infection, keloplasty, cicatrization, Crohn's disease, colitis ulcerosa, multiple sclerosis and crisis and evolution of a reverse or other reaction against dialysis.

Therefore, the 2-arylthiazole derivatives etc. according to the present invention can be used as a therapeutic agent for gout or hyperuricemia, an interleukin 1 production inhibitor and a therapeutic agent for the above-described chronic inflammatory diseases such as nephritis, hepatitis and arthritis. Further, they can be expected to exhibit, as an interleukin 1 production inhibitor, a therapeutic effect quite different from that of the conventional antifebriles and anti-inflammatory agents and antiinfectants.

EXAMPLES

The following examples only illustrate the present invention and should not be interpreted as a limitation thereof.

Example 1

390 mg of 3-Isopropoxythiobenzamide was dissolved in 5 ml of ethanol, 360 mg of ethyl 2-chloroacetoacetate was added to the solution, and the mixture was heated under reflux for five hours. After the reaction mixture was cooled, it was concentrated and subjected to silica gel chromatography (eluent, hexane: ethyl acetate=9:1) to separate an intended product (490 mg). The resulting oily substance was dissolved in 5 ml of ethanol, 10 ml of a 1N aqueous sodium hydroxide solution was added, and the mixture was heated at 70° C. for one hour. After the completion of the reaction, ethanol was removed by distillation and the residue was neutralized with 1N hydrochloric acid. The precipitated crystal was collected by filtration and recrystallized from a 50% aqueous ethanol solution to give 358 mg of 2-(3-isopropoxyphenyl)-4-methyl-5-thiazolecarboxylic acid (yield: 65%).

m.p.: 177°–179° C. $^1$H-NMR (CDCl$_3$) δ: 6.95–7.55 (m, 4H), 4.65 (m, 1H), 2.81 (s, 3H), 1.37 (d, 6H, J=6.2 Hz).

Example 2

The procedures as described in Example 1 were repeated, except that 585 mg of 4-isopropoxythiobenzamide was used instead of 3-isopropoxythiobenzamide, to give 625 mg of 2-(4-isopropoxyphenyl)-4-methyl-5-thiazolecarboxylic acid (yield: 75%).

m.p.: 186°–188° C. $^1$H-NMR (CDCl$_3$) δ: 7.89 (d, 2H, J=9.0 Hz), 6.94 (d, 2H, J=9.0 Hz), 4.62 (m, 1H), 2.79 (s, 3H), 1.38 (d, 6H, J=6.2 Hz).

Example 3

730 mg of 3-Nitrothiobenzamide was dissolved in 5 ml of ethanol, 725 mg of ethyl 2-chloroacetoacetate was added to the solution, and the mixture was heated under reflux for 18 hours. After the reaction mixture was cooled, the precipitated crystal was collected by filtration and recrystallized from a mixed solvent consisting of 10 ml of ethanol and 5 ml of ethyl acetate. 800 mg out of 898 mg of the resulting crystal was suspended in 10 ml of ethanol, 10 ml of an aqueous 1N sodium hydroxide solution was added to the suspension, and the mixture was heated at 70° C. for 2 hours. After the completion of the reaction, ethanol was removed by distillation, and the residue was neutralized with 1N hydrochloric acid. The precipitated crystal was collected by filtration and recrystallized from an aqueous 50% ethanol solution to give 560 mg of 4-methyl-2-(3-nitrophenyl)-5-thiazolecarboxylic acid (yield: 59%).

m.p.: 235°–236° C. $^1$H-NMR (DMSO d-6) δ: 8.68 (dd, 1H), 8.35 (dd, 2H), 7.80 (t, 1H), 2.81 (s, 3H).

Example 4

The procedures as described in Example 3 were repeated, except that 730 mg of 4-nitrothiobenzamide was used instead of 3-nitrothiobenzamide, to give 490 mg of 4-methyl-2-(4-nitrophenyl)-5-thiazolecarboxylic acid (yield: 51%).

m.p.: 252°–253° C. $^1$H-NMR (DMSO d-6) δ: 8.32 (d, 2H, J=9.0 Hz), 8.13 (d, 2H, J=9.0 Hz), 2.82 (s, 3H).

Compounds described in the following Examples were prepared in the same manner as that described above.

Example 5

4-Methyl-2-(3-trifluoromethylphenyl)-5-thiazolecarboxylic acid (yield: 49%).

m.p.: 171°–172° C. $^1$H-NMR (CDCl$_3$) δ: 7.49–8.27 (m, 4H), 2.83 (s, 3H).

Example 6

4-Methyl-2-(4-trifluoromethylphenyl)-5-thiazolecarboxylic acid (yield: 52%).

m.p.: about 220° C. (sublimated) $^1$H-NMR (CDCl$_3$) δ: 8.13 (d, 2H, J=8.1 Hz), 7.71 (d, 2H, J=8.1 Hz), 2.80 (s, 3H).

Example 7

2-(4-Cyclohexylmethyloxyphenyl)-4-methyl-5-thiazolecarboxylic acid (yield: 88%).

m.p.: 193°–195° C. $^1$H-NMR (CDCl$_3$) δ: 7.89 (d, 2H, J=8.8 Hz), 6.90 (d, 2H, J=8.8 Hz), 4.01 (d, 2H, J=6.2 Hz), 2.76 (s, 3H), 0.75–2.05 (m, 11H).

Example 8

2-(4-(3-Cyclohexylpropyloxy)phenyl)-4-methyl-5-thiazolecarboxylic acid (yield: 83%).

m.p.: 168°–169° C. $^1$H-NMR (CDCl$_3$) δ: 7.91 (d, 2H, J=8.8 Hz), 6.93 (d, 2H, J=8.8 Hz), 3.99 (d, 2H, J=6.3 Hz), 2.78 (s, 3H), 0.70–2.00 (m, 15H).

Example 9

2-(4-(4-Chlorobenzyloxy)phenyl)-4-methyl-5-thiazolecarboxylic acid (yield: 79%).

m.p.: 245°–246° C. $^1$H-NMR (DMSO d-6) δ: 7.91 (d, 2H, J=8.8 Hz), 7.46 (s, 4H), 7.12 (d, 2H, J=8.8 Hz), 5.19 (s, 2H), 2.65 (s, 3H).

Example 10

2-(4-(4-Fluorobenzyloxy)phenyl)-4-methyl-5-thiazolecarboxylic acid (yield: 81%).

m.p.: 251°–252° C. $^1$H-NMR (DMSO d-6) δ: 7.92 (d, 2H, J=8.8 Hz), 7.05–7.65 (m, 6H, J=8.8 Hz), 5.17 (s, 2H), 2.66 (s, 3H).

Example 11

2-(4-Carboxymethyloxyphenyl)-4-methyl-5-thiazolecarboxylic acid (yield: 79%).

m.p.: 245°–246° C.

Example 12

2-(4-(4-Carboxybutyloxy)phenyl)-4-methyl-5-thiazolecarboxylic acid (yield: 82%).

m.p.: 219°–220° C. $^1$H-NMR (DMSO d-6) δ: 7.89 (d, 2H, J=8.8 Hz), 7.03 (d, 2H, J=8.8 Hz), 4.05 (t, 2H, J=5.1 Hz), 2.66 (s, 3H), 2.30 (t, 2H, J=6.5 Hz), 1.55–1.90 (m, 6H)

Example 13

720 mg of 3-Thiocarbamoylbenzoic acid was suspended in 10 ml of dioxane, 720 mg of ethyl 2-chloroacetoacetate was added thereto, and the mixture was heated at 90° C. for 18 hours. After the reaction mixture was cooled, the resulting crystal was collected from the suspension by filtration and recrystallized from 20 ml of ethanol and a small amount of water to give 735 mg of ethyl 2-(3-carboxyphenyl)-4-methyl-5-thiazolecarboxylate (yield: 63%). 290 mg of the crystal was dissolved in 5 ml of 1N sodium hydroxide, and the mixture was heated at 60° C. for one hour. After the completion of the reaction, the reaction mixture was neutralized with 1N hydrochloric acid. The resulting crystal was collected by filtration and recrystallized from a 80% aqueous ethanol solution to give 258 mg of 2-(3-carboxyphenyl)-4-methyl-5-thiazolecarboxylic acid (yield: 83%).

m.p.: 295°–296° C. $^1$H-NMR (DMSO d-6) δ: 8.58 (s, 1H), 8.05–8.30 (m, 2H), 7.51 (t, 1H), 2.71 (s, 3H).

Example 14

2-(4-Carboxyphenyl)-4-methyl-5-thiazolecarboxylic acid was prepared from 4-thiocarbamoylbenzoic acid through an ethyl 2-(4-carboxyphenyl)-4-methyl-5-thiazolecarboxylate in the same manner as that of Example 13 (yield: 49%).

m.p.: >300° C. $^1$H-NMR (DMSO d-6) δ: 8.07 (s, 3H), 2.70 (s, 3H).

Example 15

290 mg of Ethyl 2-(3-carboxyphenyl)-4-methyl-5-thiazolecarboxylate was suspended in 2 ml of benzene, 2 ml of thionyl chloride was added to the suspension, and the mixture was heated at 80° C. for 3 hours. The reaction mixture was concentrated, and the residue was dissolved in 1,2-dichloroethane. To the solution was added a solution (5 ml) of 250 mg of p-chloroaniline in 1,2-dichloroethane, and 200 mg of triethylamine was added thereto. The mixture was heated at 80° C. for 30 minutes and cooled, and 15 ml of 1N hydrochloric acid was added thereto. The mixture was extracted twice with 30 ml of ethyl acetate. The organic layer was washed with an aqueous sodium bicarbonate solution and an aqueous saturated sodium chloride solution and evaporated to dryness, and the resulting crystal was recrystallized from a 80% aqueous ethanol solution to give 212 mg of ethyl 2-(3-(4-chlorophenylcarbamoyl)phenyl)-4-methyl-5-thiazolecarboxylate. This product was suspended in 3 ml of ethanol, hydrolyzed with 2 ml of a 1N aqueous sodium hydroxide solution and neutralized. The resulting crystal was recrystallized from aqueous ethanol solution to give 162 mg of 2-(3-(4-chlorophenylcarbamoyl)phenyl)-4-methyl-5-thiazolecarboxylic acid (yield: 43%).

m.p.: 246°–248° C.

Example 16

175 mg of 2-(4-(4-Chlorophenylcarbamoyl)phenyl)-4-methyl-5-thiazolecarboxylic acid was prepared from 290 mg of ethyl 2-(4-carboxyphenyl)-4-methyl-5-thiazolecarboxylate in the same manner as that of Example 15 (yield: 47%).

m.p.: 276°–278° C. $^1$H-NMR (DMSO d-6) δ: 10.47 (s, 1H), 8.10 (s, 4H), 7.83 (d, 2H, J=8.8 Hz), 7.40 (d, 2H, J=8.8 Hz), 2.71 (s, 3H).

Example 17

100 mg of Ethyl 2-(4-(4-chlorophenylcarbamoyl)-phenyl)-4-methyl-5-thiazolecarboxylate produced in Example 16 was methylated with sodium hydride and methyl iodide, and hydrolyzed by a conventional process to give 69 mg of 2-(4-(N-(4-chlorophenyl)-N-methylcarbamoyl)phenyl)-4-methyl-5-thiazolecarboxylic acid (yield: 72%).

m.p.: 210°–212° C. $^1$H-NMR (CDCl$_3$+CD$_3$ OD) δ: 7.78 (d, 2H, J=8.6 Hz), 7.37 (d, 2H, J=8.6 Hz), 7.21 (d, 2H, J=9.0 Hz), 7.02 (d, 2H, J=9.0 Hz), 3.48 (s, 3H), 2.74 (s, 3H).

Example 18

2-(4-(N,N-dimethylamino)phenyl)-4-methyl-5-thiazolecarboxylic acid was prepared from 4-(N,N-dimethylamino)thiobenzamide in the same manner as that of Example 1 (yield: 68%).

m.p.: 226°–231° C. $^1$H-NMR (DMSO d-6) δ: 7.77 (d, 2H, J=8.9 Hz), 6.76 (d, 2H, J=8.9 Hz), 3.00 (s, 6H), 2.62 (s, 3H).

Example 19

2-(3-Benzoylphenyl)-4-methyl-5-thiazolecarboxylic acid was prepared from 3-benzoylthiobenzamide in the same manner as that of Example 1 (yield: 57%).

m.p.: 213°–215° C. $^1$H-NMR (DMSO d-6) δ: 8.05–8.35 (m, 2H), 7.35–8.00 (m, 7H), 2.71 (s, 3H).

Example 20

2-(4-Benzoylphenyl)-4-methyl-5-thiazolecarboxylic acid was prepared from 4-benzoylthiobenzamide in the same manner as that of Example 1 (yield: 48%).

m.p.: 217°–218° C. $^1$H-NMR (DMSO d-6) δ: 8.15 (d, 2H, J=8.4 Hz), 7.85 (d, 2H, J=8.4 Hz), 7.45–7.90 (m, 5H), 2.71 (s, 3H).

Example 21

340 mg of 3-chlorothiobenzamide was dissolved in 10 ml of ethanol, 570 mg of diethyl bromomalonate was added to the solution, and the mixture was heated at 60° C. for 2 hours. After the reaction mixture was cooled, and the resulting crystal was collected by filtration and recrystallized from ethanol to give 408 mg of ethyl 2-(3-chlorophenyl)-4-hydroxy-5-thiazolecarboxylate. This product was hydrolyzed by a conventional process to give 306 mg of 2-(3-chlorophenyl)-4-hydroxy-5-thiazolecarboxylic acid (yield: 60%).

m.p.: 107°–108° C. $^1$H-NMR (DMSO d-6) δ: 7.65–8.00 (m, 2H), 7.30–7.45 (m, 2H).

Example 22

290 mg of 4-Hydroxy-2-(4-isopropoxyphenyl)-5-thiazolecarboxylic acid was prepared from 390 mg of 4-isopropoxythiobenzamide in the same manner as that of Example 21 (yield: 52%).

m.p.: 126°–127° C. $^1$H-NMR (DMSO d-6) δ: 7.99 (d, 2H, J=9.0 Hz), 7.00 (d, 2H, J=9.0 Hz), 4.72 (m, 1H, J=5.9 Hz), 1.42 (d, 6H, J =5.9 Hz).

Example 23

Ethyl 4-hydroxy-2-(4-isopropoxyphenyl)-5-thiazolecarboxylate prepared in Example 22 was methylated with sodium hydride and methyl iodide and hydrolyzed by a conventional process to give 2-(4-isopropoxyphenyl)-4-methoxy-5-thiazolecarboxylic acid (yield: 72%).

m.p.: 109°–110° C. $^1$H-NMR (DMSO d-6) δ: 7.90 (d, 2H, J=9.0 Hz), 6.91 (d, 2H, J=9.0 Hz), 4.68 (m, 1H, J=5.9 Hz), 4.23 (s, 3H), 4.23 (s, 3H), 1.39 (d, 6H, J=5.9 Hz).

The following compounds were prepared from corresponding thiobenzamides in the same manner as that of Examples 1 to 4.

Example 24

2-(2-Chloro-5-nitrophenyl)-4-methyl-5-thiazolecarboxylic acid (yield: 66%).

m.p.: 280°–285° C. $^1$H-NMR ( DMSO d-6)δ: 9.21 (d, 1H, J=2.7 Hz), 8.11 (dd, 1H, J=8.9 Hz, J=2.7 Hz), 7.59 (d, 1H, J=8.9 Hz), 2.84 (s, 3H).

Example 25

2- ( 3-Acetyl-4-hydroxyphenyl ) -4-methyl-5-thiazolecarboxylic acid (yield: 38% ).

m.p.: 251°–253° C. $^1$H-NMR (DMSO d-6) δ: 8.36 (d, 1H, J=2.2 Hz) , 8.00 (dd, 1H, J=8.7 Hz, J=2.2 Hz) , 6.96 (d, 1H, J=8.7 Hz), 2.74 (s, 3H), 3.69 (s, 3H).

Example 26

2-(3,5-Bistrifluoromethylphenyl)-4-methyl-5-thiazolecarboxylic acid (yield: 72%).

m.p.: 200° C. (sublimated) $^1$H-NMR (CDCl$_3$)δ: 8.42 (s, 2H), 7.97 (s, 1H), 2.85 (s, 3H).

Example 27

2-(3,5-Dichlorophenyl)-4-methyl-5-thiazolecarboxylic acid (yield: 77%).

m.p.: 270° C. (sublimated) $^1$H-NMR (CDCl$_3$) 8.11 (s, 2H), 7.68 (s, 1H), 2.81 (s, 3H).

Example 28

2-(3,5-Dichloro-4-hydroxyphenyl)-4-methyl-5-thiazolecarboxylic acid (yield: 64%).

m.p.: 260° C. (sublimated) $^1$H-NMR (CDCl$_3$)δ: 7.81 (s, 2H), 2.71 (s, 3H).

Example 29

2-(3,5-Di-t-butyl-4-hydroxyphenyl)-4-methyl-5-thiazolecarboxylic acid (yield: 59%).

m.p.: 261°–262° C. $^1$H-NMR (CDCl$_3$)δ: 7.80 (s, 2H), 5.58 (s, 1H), 2.79 (s, 3H), 1.49 (s, 18H).

Example 30

2-(3,5-Dimethyl-4-hydroxyphenyl)-4-methyl-5-thiazolecarboxylic acid (yield: 59%).

m.p.: 256°–257° C. $^1$H-NMR (CDCl$_3$)δ: 7.62 (s, 2H), 2.77 (s, 3H), 2.30 (s, 6H).

Example 31

(1) A mixture of 5.0 g of 4-hydroxy-3-nitrobenzaldehyde with 2.5 g of hydroxylamine hydrochloride and 3.6 g of sodium formate was heated under reflux in 35 ml of formic acid for 5 hours. After the reaction mixture was cooled, water was added thereto. The precipitated crystal was collected by filtration to give 4.3 g of 4-hydroxy-3-nitrobenzonitrile. 3.5 g of thioacetamide was added thereto and the mixture was heated at 80° C. for 1 hour in 12 ml of N,N-dimethylformamide saturated with hydrochloric acid. After the completion of the reaction, the reaction mixture was neutralized with 30 ml of water and 18 ml of 2N sodium hydroxide. The precipitated crystal was collected by filtration and recrystallized from ethanol to give 3.9 g of 4-hydroxy-3-nitrobenzthioamide. This product was dissolved in 30 ml of ethanol, 2.7 g of ethyl 2-chloroacetoacetate was added thereto, and the mixture was heated under reflux for 5 hours. The reaction mixture was cooled, and the precipitated crystal was collected by filtration and recrystallized from ethanol to give 3.4 g of ethyl 2-(4-hydroxy-3-nitrophenyl)-4-methyl-5-thiazolecarboxylate (yield: 37%).

(2) 200 mg of Ethyl 2-(4-hydroxy-3-nitrophenyl)-4-methyl-5-thiazolecarboxylate prepared in (1) was dissolved in 3 ml of N,N-dimethylformamide, 540 mg of anhydrous potassium carbonate and 440 mg of isopropyl bromide were added thereto, and the mixture was heated at 70° C. for 18 hours. After the reaction mixture was cooled, 20 ml of water was added thereto. The mixture was extracted twice with 30 ml of ethyl acetate. The organic layer was washed with a saturated aqueous sodium chloride solution, and the solvent was removed by distillation. The resulting crystal was recrystallized from ethanol to give 172 mg of ethyl 2-(4-isopropoxy-3-nitrophenyl)-4-methyl-5-thiazolecarboxylate. This product was hydrolyzed by a conventional process, and the resulting crystal was recrystallized from a 80% aqueous ethanol solution to give 135 mg of 2-(4-isopropoxy-3-nitrophenyl)-4-methyl-5-thiazolecarboxylic acid (yield:

m.p.: 211°–213° C. $^1$H-NMR (DMSO d-6) δ: 8.37 (d, 1H, J=2.2 Hz), 8.16 (dd, 1H, J=9.2 Hz, J=2.2 Hz), 7.49 (d, 1H, J=9.2 Hz), 4.93 (m, 1H, J=6.1 Hz), 2.67 (s, 3H), 1.32 (d, 6H, J=6.1 Hz).

The following compounds were produced in the same manner as that described above.

Example 32

2-(4-Cyclohexylmethyloxy-3-nitrophenyl)-4-methyl-5-thiazolecarboxylic acid (yield: 59%).

m.p.: 228°–230° C. $^1$H-NMR (DMSO d-6) δ: 8.45 (d, 1H, J=2.3 Hz), 8.10 (dd, 1H, J=8.9 Hz, J=2.3 Hz), 7.12 (d, 1H, J=8.9 Hz), 3.96 (d, 2H, J=5.7 Hz), 2.79 (s, 3H), 0.90–2.15 (m, 11H).

Example 33

2-(4-Ethoxy-3-nitrophenyl)-4-methyl-5-thiazolecarboxylic acid (yield: 59%).

m.p.: 234°–236° C. $^1$H-NMR (DMSO d-6) δ: 8.39 (d, 1H, J=2.2 Hz), 8.17 (dd, 1H, J=8.8 Hz, J=2.2 Hz), 7.46 (d, 1H, J=8.8 Hz), 4.31 (q, 2H, J=7.0 Hz), 2.67 (s, 3H), 1.38 (t, 3H, J=7.0 Hz).

Example 34

2-(4-Isobutyloxy-3-nitrophenyl)-4-methyl-5-thiazolecarboxylic acid (yield: 42%).

m.p.: 210°–212° C. $^1$H-NMR (CDCl$_3$) δ: 8.45 (d, 1H, J=2.2 Hz), 8.11 (dd, 1H, J=8.8 Hz, J=2.2 Hz), 7.13 (d, 1H, J=8.8 Hz), 3.94 (d, 2H, J=6.8 Hz), 2.80 (s, 3H), 2.00–2.35 (m, 1H), 1.17 (d, 6H, J=6.8 Hz).

Example 35

2.9 g of Ethyl 2-(4-chloro-3-nitrophenyl)-4-methyl-5-thiazolecarboxylate was prepared from 3.4 g of 4-chloro-3-nitrobenzaldehyde in the same manner as that of Example 31 (yield: 48%). 330 mg of this product was weighed and dissolved in 5 ml of ethanol, 200 mg of anhydrous potassium carbonate and 80 mg of 2-mercaptopropane were added thereto, and the mixture was heated at 80° C. for 2 hours. After the completion of the reaction, ethanol was removed by distillation, 20 ml of water was added thereto, and the mixture was extracted twice with 30 ml of ethyl acetate. After the organic layer was washed with an aqueous saturated sodium chloride solution, the solvent was removed by distillation. The resulting crystal was recrystallized from ethanol to give 213 mg of ethyl 2-(4-isopropylthio-3-nitrophenyl)-4-methyl-5-thiazolecarboxylate. This product was hydrolyzed by a conventional process, and the resulting crystal was recrystallized from ethanol to give 162 mg of 2-(4-isopropylthio-3-nitrophenyl)-4-methyl-5-thiazolecarboxylic acid (yield: 48%).

m.p.: 233°–235° C. $^1$H-NMR (DMSO d-6) δ: 8.64 (d, 1H, J=2.1 Hz), 8.03 (dd, 1H, J=8.5 Hz, J=2.1 Hz), 7.44 (d, 1H, J=8.5 Hz), 3.59 (m, 1H, J=6.6 Hz), 2.74 (s, 3H), 1.39 (d, 6H, J=6.6 Hz).

Example 36

Ethyl 2-(4-chloro-3-nitrophenyl)-4-methyl-5-thiazolecarboxylate was reacted with 4-chlorothiophenol in the same manner as that of Example 35 to give 2-(4-(4-chlrophenyl)thio-3-nitrophenyl)-4-methyl-5thiazolecarboxylic acid (yield: 65%).

m.p.: 250° C. (sublimated) $^1$H-NMR (DMSO d-6) δ: 8.74 (d, 1H, J=2.0 Hz), 8.08 (dd, 1H, J=8.8 Hz, J=2.0 Hz), 7.66 (s, 4H), 7.00 (d, 1H, J=8.8 Hz), 2.68 (s, 3H).

Example 37

Ethyl 2-(4-chloro-3-nitrophenyl)-4-methyl-5-thiazolecarboxylate in diethylamine was heated in the same manner as that of Example 35 and hydrolyzed to give 2-(4-N,N-diethylamino)-3-nitrophenyl)-4-methyl-5-thiazolecarboxylic acid (yield: 56%).

m.p.: 208°–210° C. $^1$H-NMR (DMSO d-6) δ: 8.24 (d, 1H, J=2.2 Hz), 7.84 (dd, 1H, J=8.9 Hz, J=2.2 Hz), 7.02 (d, 1H, J=8.9 Hz), 3.21 (q, 4H), 2.66 (s, 3H), 1.10 (t, 6H).

Example 38

Ethyl 2-(4-chloro-3-nitrophenyl)-4-methyl-5-thiazolecarboxylate in pyrrolidine was heated in the same manner as that of Example 37 and hydrolyzed to give 2-(4-morpholino-3-nitrophenyl)-4-methyl-5-thiazolecarboxylic acid (yield: 57%).

m.p.: 218°–220° C. $^1$H-NMR ( DMSO d-6 ) δ: 8.26 (d, 1H, J=2.2 Hz), 7.95 (dd, 1H, J=9.0 Hz, J=2.2 Hz), 7.12 (d, 1H, J=9.0 Hz), 3.05–3.45 (m, 4H), 2.65 (s, 3H), 1.70–2.30 (m, 4H).

Compounds of Examples 39 to 42 were prepared in the same manner as that of Example 31.

Example 39

2-(4-(2-Ethoxyethyloxy)-3-nitrophenyl)-4-methyl-5-thiazolecarboxylic acid (yield: 73%).

m.p.: 197°–199° C. (decomposed) $^1$H-NMR ( DMSO d-6 ) δ: 8.45 (d, 1H, J=2.4 Hz), 8.10 (dd, 1H, J=8.8 Hz, J=2.4 Hz), 7.20 (d, 1H, J=8.8 Hz), 4.35 (t, 2H, J=4.8 Hz), 3.86 (t, 2H, J=4.8 Hz), 3.63 (q, 2H, J=7.0 Hz), 2.79 (s, 3H), 1.23 (t, 3H, J=7.0 Hz).

Example 40

2-(4-Isopentyloxy-3-nitrophenyl)-4-methyl-5-thiazolecarboxylic acid (yield: 68%).

m.p.: 217°–219° C. $^1$H-NMR (CDCl$_3$) δ: 8.41 (d, 1H, J=2.2 Hz), 8.09 (dd, 1H, J=8.8 Hz, J=2.2 Hz), 7.13 (d, 1H, J=8.8 Hz), 4.20 (t, 2H, J=6.4 Hz), 2.77 (s, 3H), 1.6–2.0 (m, 3H), 0.98 (d, 6H, J=5.9 Hz).

Example 41

2-(4-n-Hexyloxy-3-nitrophenyl)-4-methyl-5-thiazolecarboxylic acid (yield: 62%).

m.p.: 194°–195° C. $^1$H-NMR (DMSO-d$_6$) δ: 8.41 (d, 1H, J=2.2 Hz), 8.19 (dd, 1H, J=9.0 Hz, J=2.2 Hz), 7.47 (d, 1H, J=9.0 Hz), 4.24 (t, 2H, J=6.2 Hz), 2.67 (s, 3H), 0.75–1.97 (m, 11H).

Example 42

2-(4-(2-Ethylbutyloxy)-3-nitrophenyl)-4-methyl-5-thiazolecarboxylic acid (yield: 59%).

m.p.: 230°–231° C. $^1$H-NMR (DMSO-d$_6$) δ: 8.41 (d, 1H, J=2.0 Hz), 8.19 (dd, 1H, J=8.8 Hz, J=2.0 Hz), 7.50 (d, 1H, J=8.8 Hz), 4.15 (d, 2H, J=5.7 Hz), 2.68 (s, 3H), 1.1–1.9 (m, 5H), 0.91 (t, 6H, J=6.6 Hz).

Example 43

1.83 g of 4-Chloro-3-nitrobenzonitrile and 1.06 g of neopentyl alcohol were dissolved in 10 ml of N,N-dimethylformamide. The solution was cooled to 0° C., and 480 mg of sodium hydride (60% in oil) was gradually added thereto. Then, 30 min after the addition, 13 ml of 1N hydrochloric acid was added to the mixture, and the precipitated crystal was collected by filtration to give 2.12 g of 4-neopentyloxy-3-nitrobenzonitrile. 1.2 g of thioacetamide was added thereto, and the mixture was heated at 80° C. for an hour in N,N-dimethylformamide saturated with hydrochloric acid. After the completion of the reaction, the reaction mixture was neutralized with 30 ml of water and 18 ml of 2N sodium hydroxide, and the lower layer was separated and dried. The lower layer was dissolved in 30 ml of ethanol, 2.11 g of ethyl 2-chloroacetoacetate was added thereto, and the mixture was heated under reflux for 5 hours. After the reaction mixture was cooled, the precipitated crystal was collected by filtration and recrystallized from ethanol to give 2.38 g of ethyl 4-methyl-2-(4-neopentyloxy-3-nitrophenyl)-5-thiazolecarboxylate (yield: 63%). This product was hydrolyzed by a conventional process, and the resulting crystal was recrystallized from a 80% aqueous ethanol solution to give 1.98 g of 2-(4-neopentyloxy-3-nitrophenyl)-4-methyl-5-thiazolecarboxylic acid (yield:

m.p.: 242°–245° C. $^1$H-NMR (CDCl$_3$) δ: 8.47 (d, 1H, J=2.2 Hz), 8.15 (dd, 1H, J=8.8 Hz, J=2.3 Hz), 7.12 (d, 1H, J=8.8 Hz), 3.80 (s, 2H), 2.80 (s, 3H), 1.09 (s, 9H).

Example 44

As described in Example 37, ethyl 2-(4-chloro-3-nitrophenyl)-4-methyl-5-thiazolecarboxylate was reacted in piperidine, and the resulting ethyl 4-methyl-2-(3-nitro-4-piperidinophenyl)-5-thiazolecarboxylate was hydrolyzed by a conventional process to give 135 mg of 4-methyl-2-(3-nitro-4-piperidinophenyl)-5-thiazolecarboxylic acid (yield: 63%).

m.p.: 249°–251° C. (decomposed) $^1$H-NMR (DMSO-d$_6$) δ: 8.30 (d, 1H, J=2.2 Hz), 8.01 (dd, 1H, J=8.8 Hz, J=2.2 Hz), 7.31 (d, 1H, J=8.8 Hz), 3.0–3.3 (m, 4H), 2.66 (s, 3H), 1.5–1.8 (m, 6H).

Example 45

As described in Example 37, ethyl 2-(4-chloro-3-nitrophenyl)-4-methyl- 5-thiazolecarboxylate was reacted in morpholine, and the resulting ethyl 4-methyl-2-(4-morpholino-3-nitrophenyl)-5-thiazolecarboxylate was hydrolyzed by a conventional process to give 4-methyl-2(4-morpholino-3-nitrophenyl)-5-thiazolecarboxylic acid (yield: 71%).

m.p.: 251°–252° C. ¹H-NMR (DMSO-d$_6$) δ: 8.35 (d, 1H, J=2.2 Hz), 8.08 (dd, 1H, J=8.8 Hz, J=2.2 Hz), 7.36 (d, 1H, J=8.8 Hz), 3.6–3.9 (m, 4H), 3.0–3.3 (m, 4H), 2.67 (s, 3H).

Example 46

As described in Example 37, ethyl 2-(4-chloro-3-nitrophenyl)-4-methyl-5-thiazolecarboxylate was reacted in 1-methylpiperazine, and the resulting ethyl 4-methyl-2-(4-(4-methylpiperazinyl)-3-nitrophenyl)-5-thiazolecarboxylate was hydrolyzed by a conventional process to give 4-methyl-2-(4-(4-methylpiperazinyl)-3-nitrophenyl)-5-thiazolecarboxylic acid (yield: 58%).

m.p.: 218°–220° C. ¹H-NMR (DMSO-d$_6$) δ: 8.33 (d, 1H, J=2.2 Hz), 8.05 (dd, 1H, J=8.8 Hz, J=2.2 Hz), 7.37 (d, 1H, J=8.8 Hz), 2.9–3.4 (m, 4H), 2.66 (s, 3H), 2.3–2.7 (m, 4H), 2.29 (s, 3H).

Example 47

200 mg of Ethyl 2-(4-chloro-3-nitrophenyl)-4-methyl-5-thiazolecarboxylate was suspended in 5 ml of isopropyl alcohol, and 60 mg of sodium hydride (60% in oil) was added thereto at room temperature. After 20 hours of the addition, 20 ml of water was added to the mixture, the precipitated crystal was collected by filtration, and recrystallized from ethanol to give 165 mg of isopropyl 2-(4-isopropoxy-3-nitrophenyl)-4-methyl-5-thiazolecarboxylate (yield: 74%).

m.p.: 91°–92° C. ¹H-NMR (CDCl$_3$) δ: 8.37 (d, 1H, J=2.2 Hz), 8.07 (dd, 1H, J=8.9 Hz, J=2.2 Hz), 7.15 (d, 1H, J=8.9 Hz), 5.1–5.4 (m, 1H), 4.6–4.9 (m, 1H), 2.76 (s, 3H), 1.2–1.6 (m, 12H).

Example 48

160 mg of Isobutyl 2-(4-isobutyloxy-3-nitrophenyl)-4-methyl-5-thiazolecarboxylate was prepared from 200 mg of ethyl 2-(4-chloro-3-nitrophenyl)-4-methyl-5-thiazolecarboxylate in the same manner as that of Example 47 (yield: 67%).

m.p.: 112°–113° C. ¹H-NMR (CDCl$_3$) δ: 8.43 (d, 1H, J=2.2 Hz), 8.10 (dd, 1H, J=8.8 Hz, J=2.2 Hz), 7.11 (d, 1H, J=8.8 Hz), 4.09 (d, 2H, J=6.6 Hz), 3.93 (d, 2H, J=6.4 Hz), 2.77 (s, 3H), 1.9–2.4 (m, 2H), 0.9–2.2 (m, 12H).

Example 49

(1) 5.0 g of Ethyl 2-(4-hydroxy-3-nitrophenyl)-4-methyl-5-thiazolecarboxylate was dissolved in 120 ml of ethanol and 60 ml of ethyl acetate, and 2 ml of concentrated hydrochloride and 500 mg of a 10% palladium/carbon was added thereto, and the mixture was stirred under a hydrogen atmosphere for 24 hours. After the completion of the reaction, methanol and water were added thereto, the mixture was filtered, and the filtrate was concentrated. The resulting crystal was suspended in 25 ml of 2N hydrochloric acid and 25 ml of acetone, and a solution of 1.2 g of sodium nitrite in 8 ml of water was gradually added thereto with ice cooling. Separately, 2.2 g of cuprous chloride was suspended in 15 ml of 2N hydrochloric acid and the diazonium salt solution was gradually added thereto with ice cooling. After the completion of the dropwise addition, the reaction mixture was heated to 60° C., and one hour after the heating, 100 ml of water was added thereto. The precipitated crystal was collected by filtration. This product was purified by silica gel chromatography to give 4.4 g of ethyl 2-(3-chloro-4-hydroxyphenyl)-4-methyl-5-thiazolecarboxylate (yield: 91%).

(2) 300 mg of the Phenol derivative produced in (1) was suspended in 5 ml of N,N-dimethylformamide, 690 mg of anhydrous potassium carbonate and 550 mg of ethyl bromide were added thereto, and the mixture was stirred at 70° C. for 24 hours. After the completion of the reaction, the reaction product was poured into water, and the mixture was extracted with ether. The organic layer was concentrated to give a crystalline product. This product was hydrolyzed by a conventional process and purified by recrystallization to give 230 mg of 2-(3-chloro-4-ethoxyphenyl)-4-methyl-5-thiazolecarboxylic acid (yield: 71%).

m.p.: 219°–220° C. ¹H-NMR (DMSO-d$_6$) δ: 7.96 (d, 1H, J=2.4 Hz), 7.82 (dd, 1H, J=8.6 Hz, J=2.4 Hz), 7.23 (d, 1H, J=8.6 Hz), 4.20 (q, 2H, J=7.0 Hz), 2.66 (s, 3H), 1.40 (t, 3H, J=7.0 Hz).

The following compounds were prepared in the same manner as that described above.

Example 50

2-(3-Chloro-4-isopropoxyphenyl)-4-methyl-5-thiazolecarboxylic acid (yield: 65%).

m.p.: 199°–200° C. ¹H-NMR (DMSO-d$_6$) δ: 7.98 (d, 1H, J=2.2 Hz) 7.68 (dd, 1H, J=8.8 Hz, J=2.2 Hz) 7.26 (d, 1H, J=8.8 Hz) 4.78 (8, 1H, J=6.2 Hz) 2.66 (S, 3H) 1.34 (d, 6H, J=6.2 Hz).

Example 51

2-(3-Chloro-4-isobutyloxyphenyl)-4-methyl-5-thiazolecarboxylic acid (yield: 58%).

m.p.: 182°–183° C. ¹H-NMR (DMSO-d$_6$) δ: 7.98 (d, 1H, J=2.0 Hz), 7.87 (dd, 1H, J=8.4 Hz, J=2.0 Hz), 7.23 (d, 1H, J=8.4 Hz), 3.92 (d, 2H, J=6.4 Hz), 2.66 (s, 3H), 1.9–2.3 (m, 1H), 1.03 (d, 6H, J=6.6 Hz).

Example 52

2-(3-Chloro-4-isopentyloxyphenyl)-4-methyl-5-thiazolecarboxylic acid (yield: 67%).

m.p.: 165°–166° C. ¹H-NMR (DMSO-d$_6$) δ: 7.98 (d, 1H, J=2.0 Hz), 7.88 (dd, 1H, J=8.6 Hz, J=2.0 Hz), 7.26 (d, 1H, J=8.6 Hz), 4.17 (t, 2H, J=6.4 Hz), 2.66 (s, 3H), 1.5–1.9 (m, 3H), 0.96 (d, 6H, J=5.9 Hz).

Example 53

2-(3-Chloro-4-(2-ethylbutyloxy)phenyl)-4-methYl-5-thiazolecarboxylic acid (yield: 62%).

m.p.: 154°–156° C. ¹H-NMR (DMSO-d$_6$) δ: 7.97 (d, 1H, J=2.0 Hz), 7.87 (dd, 1H, J=8.6 Hz, J=2.0 Hz), 7.26 (d, 1H, J=8.6 Hz), 4.04 (d, 2H, J=5.1 Hz), 2.66 (s, 3H), 1.3–1.8 (m, 5H), 0.92 (d, 6H, J=7.0 Hz).

Example 54

2-(3-Chloro-4-neopentyloxyphenYl)-4-methyl-5-thiazolecarboxylic acid (yield: 49%).

m.p.: 218°–220° C. ¹H-NMR (DMSO-d$_6$) δ: 7.98 (d, 1H, J=2.2 Hz), 7.87 (dd, 1H, J=8.6 Hz, J=2.2 Hz), 7.21 (d, 1H, J=8.6 Hz), 3.79 (s, 2H), 2.66 (s, 3H), 1.05 (m, 9H).

Example 55

2-(3-Chloro-4-(2-ethoxyethyloxy)phenyl)-4-methyl-5-thiazolecarboxylic acid (yield: 51%).

m.p.: 147°–148° C. ¹H-NMR (DMSO-d$_6$) δ: 7.99 (d, 1H, J=2.2 Hz), 7.88 (dd, 1H, J=8.6 Hz, J=2.2 Hz), 7.27 (d, 1H, J=8.6 Hz), 4.2–4.4 (m, 2H), 3.7–3.9 (m, 2H), 3.55 (q, 2H, J=6.8 Hz), 2.66 (s, 3H), 1.14 (t, 3H, J=6.8 Hz).

Example 56

2-(3-Chloro-4-(2-morpholinoethyloxy)phenyl)-4-methyl-5-thiazolecarboxylic acid (yield: 57%).

m.p.: 207°–209° C. ¹H-NMR (DMSO-d$_6$) δ: 7.98 (d, 1H, J=2.0 Hz), 7.87 (dd, 1H, J=8.6 Hz, J=2.0 Hz), 7.27 (d, 1H, J=8.6 Hz), 4.27 (t, 2H, J=5.6 Hz), 3.5–3.7 (m, 4H), 2.79 (t, 2H, J=5.6 Hz), 2.66 (s, 3H), 2.4–2.7 (m, 4H).

Example 57

2-(3-Chloro-4-(2-piperidinoethyloxy)phenyl)-4-methyl-5-thiazolecarboxylic acid (yield: 49%).

m.p.: 240°–243° C. (decomposed) ¹H-NMR (DMSO-d$_6$) δ: 7.94 (d, 1H, J=2.0 Hz), 7.81 (dd, 1H, J=8.6 Hz, J=2.0 Hz), 7.25 (d, 1H, J=8.6 Hz), 4.32 (t, 2H, J=5.5 Hz), 2.94 (t, 2H, J=5.5 Hz), 2.66 (s, 3H), 2.5–2.8 (m, 4H), 1.3–1.8 (m, 6H).

Example 58

2-(3-Chloro-4-(4-fluorobenzyloxy)phenyl)-4-methyl-5-thiazolecarboxylic acid (yield: 63%).

m.p.: 260°–265° C. (sublimated) ¹H-NMR (DMSO-d$_6$) δ: 8.01 (d, 1H, J=2.2 Hz), 7.90 (dd, 1H, J=8.6 Hz, J=2.2 Hz), 7.1–7.7 (m, 5H), 5.28 (s, 2H), 2.66 (s, 3H).

Example 59

(1) 4.6 g of Ethyl 2-(4-chloro-3-nitrophenyl)-4-methyl-5-thiazolecarboxylate was prepared from 5.0 g of 4-chloro-3-nitrobenzaldehyde in the same manner as that of Example 31 (yield: 51%). This product was taken up in 10 ml of morpholine, and stirred for 2 hours, to the mixture was added 30 ml of water, and the precipitated crystal was collected by filtration. The resulting crystal was recrystallized from ethanol to give 1.02 g of ethyl 4-methyl-2-(4-morpholino-3-nitrophenyl)-5-thiazolecarboxylate (yield: 89%).

(2) 1.0 g of Ethyl 4-methyl-2-(4-morpholino-3-nitrophenyl)-5-thiazolecarboxylate thus obtained, was suspended in 80 ml of ethanol, and to the suspension was added 200 mg of 10% palladium/carbon, followed by stirring in a hydrogen atmosphere. After seven hours, the catalyst was removed by filtration, and the filtrate was concentrated to give a crystalline product. The resulting product was suspended in 10 ml of 5N hydrochloric acid and 10 ml of acetone, and to the suspension was gradually added 180 mg of sodium nitrite. Separately, 340 mg of cuprous chloride was suspended in 5 ml of 2N hydrochloric acid, and the diazonium solution was gradually dropwise added thereto with ice cooling. After completion of the dropwise addition, the reaction mixture was heated to 60° C. for 30 minutes with stirring, water was added to the reaction mixture, and the precipitated crystal was collected by filtration. This product was purified by silica gel chromatography to give 520 mg of ethyl 2-(3-chloro-4-morpholinophenyl)-4-methyl-5-thiazolecarboxylate. This compound was hydrolyzed by a conventional process. Recrystallization from acetone-H$_2$O afforded 240 mg of 2-(3-chloro-4-morpholinophenyl)-4-methyl-5-thiazolecarboxylic acid (yield: 27%).

m.p.: 228°–229° C. (decomposed) ¹H-NMR (CDCl$_3$+ CD$_3$OD) δ: 7.89 (d, 1H, J=2.2 Hz), 7.72 (d, 1H, J=8.4 Hz, J=2.2 Hz), 7.05 (d, 1H, J=8.4 Hz), 3.7–3.9 (m, 4H), 2.9–3.1 (m, 4H), 2.64 (s, 3H).

The following compounds were prepared in the same manner as that described above.

Example 60

2-(3-Chloro-4-piperidinophenyl)-4-methyl-5-thiazolecarboxylic acid (yield: 19%).

m.p.: 227°–230° C. (decomposed) ¹H-NMR (DMSO-d$_6$) δ: 7.94 (d, 1H, J=2.0 Hz), 7.84 (dd, 1H, J=8.1 Hz, J=2.0 Hz), 7.19 (d, 1H, J=8.1 Hz), 2.9–3.2 (m, 4H), 2.66 (s, 3H), 1.5–1.8 (m, 6H).

Example 61

2-(3-Chloro-4-(4-chlorophenylthio)phenyl)-4-methyl-5-thiazolecarboxylic acid (yield: 32%).

m.p.: 238°–240° C. ¹H-NMR (DMSO-d$_6$) δ: 8.05 (d, 1H, J=1.8 Hz), 7.80 (dd, 1H, J=8.4 Hz, J=1.8 Hz), 7.55 (s, 4H), 6.99 (d, 1H, J=8.4 Hz), 2.66 (s, 3H).

Example 62

350 mg of Ethyl 2-(3-chloro-4-(4-chlorophenylthio)phenyl)-4-methyl-5-thiazolecarboxylate, which was an intermediate in Example 61, was suspended in 5 ml of acetic acid, and 3 ml of 30% aqueous hydrogen peroxide solution was added thereto, followed by stirring for 5 hours. After completion of the reaction, water was added to the reaction mixture, the precipitated crystal was collected by filtration, and the product was purified by silica gel chromatography, and hydrolyzed by a conventional process to give 85 mg of 2-(3-chloro-4-(4'-chlorophenylsulfinyl)phenyl)-4-methyl-5thiazolecarboxylic acid (yield: 26%).

m.p.: 257°–259° C. ¹H-NMR (DMSO-d$_6$) δ: 8.0–8.4 (m, 3H), 7.70 (q, 4H, J=8.8 Hz), 2.68 (s, 3H).

Example 63

(1) 5.0 g of Ethyl 2-(4-hydroxy-3-nitrophenyl)-4-methyl-5-thiazolecarboxylate was dissolved in 120 ml of ethanol and 60 ml of ethyl acetate, 500 mg of a 10% palladium/carbon was added thereto, and the mixture was stirred in a hydrogen atmosphere at room temperature for 24 hours. After the completion of the reaction, chloroform was added thereto, the mixture was filtered, and the filtrate was concentrated. The resulting crystal was suspended in 2 ml of hydrobromic acid, 10 ml of water and 25 ml of acetone, and a solution of 1.2 g of sodium nitrite in 8 ml of water was gradually added thereto with ice cooling. Separately, 2.2 g of cuprous bromide was suspended in 2 ml of hydrobromic acid and 10 ml of water, and the diazonium salt solution was gradually added dropwise thereto with ice cooling. After the completion of the dropwise addition, the reaction mixture was heated to 60° C., and one hour after the heating, 100 ml of water was added thereto. The precipitated crystal was collected by filtration. This product was purified by silica gel chromatography to give 3.6 g of ethyl 2-(3-bromo-4-hydroxyphenyl)-4-methyl-5-thiazolecarboxylate (yield: 65%).

(2) 340 mg of the phenol derivative prepared in step (1) was suspended in 5 ml of N,N-dimethylformamide, 690 mg of anhydrous potassium carbonate and 690 mg of isobutyl bromide were added thereto, and the mixture was stirred at 70° C. for 24 hours. After the completion of the reaction, the reaction product was poured into water, and the mixture was extracted with ether. The organic layer was concentrated to give a crystalline product. This product was hydrolyzed by a conventional process and purified by recrystallization to give 310 mg of 2-(3-bromo-4-isobutyloxyphenyl)-4-methyl-5-thiazolecarboxylic acid (yield: 78%).

m.p.: 200°–202° C. $^1$H-NMR (DMSO-$d_6$) δ: 8.18 (d, 1H, J=2.2 Hz), 7.88 (dd, 1H, J=8.6 Hz, J=2.2 Hz), 7.19 (d, 1H, J=8.6 Hz), 3.89 (d, 2H, J=6.4 Hz), 2.66 (s, 3H), 2.0–2.3 (m, 1H), 1.03 (d, 6H, J=6.4 Hz).

The following compounds were prepared in the same manner as that described above.

Example 64

2-(3-Bromo-4-(2-ethoxyethyloxy)phenyl)-4-methyl-5-thiazolecarboxylic acid (yield: 59%).

m.p.: 163°–164° C. $^1$H-NMR (DMSO-$d_6$) δ: 8.14 (d, 1H, J=2.0 Hz), 7.91 (dd, 1H, J=8.8 Hz, J=2.2 Hz), 7.23 (d, 1H, J=8.8 Hz), 4.2–4.4 (m, 2H), 3.7–3.9 (m, 2H), 3.56 (q, 2H, J=7.0 Hz), 2.66 (s, 3H), 1.14 (t, 3H, J=6.8 Hz).

Example 65

2-(3-Bromo-4-(4-chlorophenylthio)phenyl)-4-methyl-5-thiazolecarboxylic acid. (yield: 28%).

m.p.: 232°–234° C. $^1$H-NMR (DMSO-$d_6$) δ: 8.20 (d, 1H, J=1.8 Hz), 7.83 (dd, 1H, J=8.4 Hz, J=1.8 Hz), 7.56 (s, 3H), 6.93 (d, 1H, J=8.4 Hz), 2.66 (s, 3H).

Example 66

2-(3-Bromo-4-piperidinophenyl)-4-methyl-5-thiazolecarboxylic acid (yield: 29%).

m.p.: 221°–224° C. (decomposed) $^1$H-NMR (DMSO-$d_6$) δ: 8.11 (d, 1H, J=2.0 Hz), 7.87 (dd, 1H, J=8.3 Hz, J=2.0 Hz), 7.17 (d, 1H, J=8.3 Hz), 2.8–3.2 (m, 4H), 2.66 (s, 3H), 1.5–1.9 (m, 6H).

Example 67

330 mg of Ethyl 2-(3-amino-4-isobutyloxyphenyl)-4-methyl-5-thiazolecarboxylate was dissolved in 15 ml of methylene chloride, 130 mg of nitronium tetrafluoroborate was added thereto with ice cooling, followed by stirring for 4 hours. The reaction mixture was concentrated, irradiated with a UV lamp at 300 nm for 20 hours and purified by silica gel chromatography to give 175 mg of ethyl 2-(3-fluoro-4-isobutyloxyphenyl)-4-methyl-5-thiazolecarboxylate. This product was hydrolyzed by a conventional process and recrystallized from acetone-water to give 108 mg of 2-(3-fluoro-4-isobutyloxyphenyl)-4-methyl-5-thiazolecarboxylic acid (yield: 35%).

$^1$H-NMR (DMSO-$d_6$) δ: 7.6–8.0 (m, 2H), 6.8–7.0 (m, 1H), 3.83 (d, 2H, J=6.4 Hz), 2.70 (s, 3H), 2.0–2.3 (m, 1H), 1.05 (d, 6H, J=6.6 Hz).

Example 68

3.2 g of Ethyl 2-(3,5-dichloro-4-hydroxyphenyl)-4-methyl-5-thiazolecarboxylate was prepared from 3.8 g of 3,5-dichloro-4-hydroxybenzonitrile in the same manner as that of Example 31 (yield: 48%). 330 mg of this product was weighed and suspended in 5 ml of N,N-dimethylformamide, 700 mg of anhydrous potassium carbonate and 620 mg of isopropyl bromide were added thereto, and the mixture was stirred at 70° C. for 24 hours. After the completion of the reaction, the reaction mixture was poured into water and extracted with ether. The organic layer was concentrated to give a crystalline product. This product was hydrolyzed by a conventional process and purified by recrystallization to give 250 mg of 2-(3,5-dichloro-4-isopropoxyphenyl)-4-methyl-5-thiazolecarboxylic acid (yield: 67%).

m.p.: 189°–191° C. $^1$H-NMR (DMSO-$d_6$) δ: 8.03 (s, 2H), 4.66 (q, 1H, J=6.2 Hz), 2.67 (s, 3H), 1.34 (d, 6H, J=6.2 Hz).

The following compounds were prepared in the same manner as that described above.

Example 69

2-(3,5-Dichloro-4-isobutyloxyphenyl)-4-methyl-5-thiazolecarboxylic acid (yield: 54%).

m.p.: 220°–230° C. (decomposed) $^1$H-NMR (DMSO-$d_6$) δ: 8.01 (s, 2H), 3.83 (d, 2H, J=6.2 Hz), 2.67 (s, 3H), 2.0–2.3 (m, 1H), 1.05 (d, 6H, J=6.6 Hz).

Example 70

2-(3,5-Dichloro-4-(2-ethylbutyloxy)phenyl)-4-methyl-5-thiazolecarboxylic acid (yield: 69%).

m.p.: 189°–191° C. (decomposed) $^1$H-NMR (DMSO-$d_6$) δ: 8.00 (s, 2H), 3.95 (d, 2H, J=6.2 Hz), 2.67 (s, 3H), 1.3–1.7 (m, 5H), 0.95 (t, 6H, J=6.8 Hz).

Example 71

2-(3,5-Dichloro-4-isopentyloxyphenyl)-4-methyl-5-thiazolecarboxylic acid (yield: 59%).

m.p.: 193°–194° C. $^1$H-NMR (DMSO-$d_6$) δ: 8.00 (s, 2H), 4.08 (t, 2H, J=6.6 Hz), 2.67 (s, 3H), 1.5–2.0 (m, 3H), 0.95 (d, 6H, J=6.2 Hz).

Example 72

2-(3,5-Dichloro-4-(2-morpholinoethyloxy)phenyl)-4-methyl-5-thiazolecarboxylic acid (yield: 58%).

m.p.: 238°–240° C. (decomposed) $^1$H-NMR (DMSO-$d_6$) δ: 8.00 (s, 2H), 4.21 (t, 2H, J=5.7 Hz), 3.4–3.6 (m, 4H), 2.79 (t, 2H, J=5.7 Hz), 2.67 (s, 3H), 2.4–2.6 (m, 4H).

Example 73

(1) 3.46 g of Ethyl 2-(4-carboxyphenyl)-4-methyl-5-thiazolecarboxylate was prepared from 5.0 g of 4-cyanobenzoic acid in the same manner as that of Example 31 (yield: 35%).

(2) 1.0 g of this product was weighed and suspended in 20 ml of benzene, 5 ml of thionyl chloride was added thereto, and a reaction was allowed to react at 80° C. for 4 hours. The reaction mixture was evaporated to dryness and again suspended in 30 ml of benzene. 1.15 g of aluminum chloride was added to the suspension, and the mixture was stirred at 60° C. for 1 hour. After the completion of the reaction, the reaction product was decomposed with 30 g of ice water and extracted twice with 50 ml of ethyl acetate. The organic layer was washed with an aqueous saturated sodium chloride solution and then concentrated. The resulting crystal was recrystallized from ethanol to give 750 mg of ethyl 2-(4-benzoylphenyl)-4-methyl-5-thiazolecarboxylate. This product was hydrolyzed by a conventional process and recrystallized from ethanol to give 585 mg of 2-(4-benzoylphenyl)-4-methyl- 5-thiazolecarboxylic acid (yield: 53%).

m.p.: 217°–218° C. $^1$H-NMR (DMSO-d$_6$) δ: 8.15 (d, 2H, J=8.4 Hz), 7.85 (d, 2H, J=8.4 Hz), 7.45–7.90 (m, 5H), 2.71 (s, 3H).

The following compounds were prepared in the same manner as that described above.

Example 74

4-Methyl-2-(4-(4-methylbenzoyl)phenyl)-5-thiazolecarboxylic acid (yield: 21%).

m.p.: 263°–265° C. $^1$H-NMR (CDCl$_3$s) δ: 8.14 (d, 2H, J=8.6 Hz), 7.82 (d, 2H, J=8.6 Hz), 7.69 (d, 2H, J=8.4 Hz), 7.38 (d, 2H, J=8.4 Hz), 2.71 (s, 3H), 2.43 (s, 3H).

Example 75

2-(4-(2,4-Dimethylbenzoyl)phenyl)-4-methyl-5-thiazolecarboxylic acid (yield: 21%).

m.p.: 184°–186° C. $^1$H-NMR (CDCl$_3$) δ: 8.07 (d, 2H, J=8.6 Hz), 7.80 (d, 2H, J=8.6 Hz), 7.0–7.4 (m, 3H), 2.72 (s, 3H), 2.32 (s, 3H), 2.20 (s, 3H).

Example 76

1.0 g of Ethyl 2-(4-isopropoxy-3-nitrophenyl)-4-methyl-5-thiazolecarboxylate was dissolved in 20 ml of ethanol and 20 ml of ethyl acetate, 100 mg of a 10% palladium/carbon was added thereto, and the mixture was stirred in a hydrogen atmosphere at room temperature for 24 hours. After completion of the reaction, the catalyst was removed by filtration from the reaction mixture, and the filtrate was concentrated. The resulting crystal was dissolved in 4 ml of concentrated hydrochloric acid, the solution of 215 mg of sodium nitrite in 3 ml of water was gradually added dropwise thereto with ice cooling, and 30 minutes after the dropwise addition, the reaction mixture was neutralized with 40 ml of aqueous saturated sodium bicarbonate solution. Separately, 620 mg of cuprous cyanide and 400 mg of potassium cyanide were suspended in 10 ml of water, the suspension was stirred at 70° C., and then ice cooled, and to the suspension was gradually dropwise added the diazonium salt solution with ice cooling. After the completion of the dropwise addition, the reaction mixture was heated to 60° C. for one hour, following by extraction with 100 ml of ethyl acetate. The organic layer was concentrated to give a residue, and the residue was purified by silica gel chromatography to give 400 mg of ethyl 2-(3-cyano-4-isopropoxyphenyl)-4-methyl-5-thiazolecarboxylate (yield: 42%).

This product was dissolved in 3 ml of ethanol and 4 ml of tetrahydrofuran, 2 ml of 1N sodium hydroxide was added thereto, and hydrolysis effected by heating to 60° C. for one hour. The solvent was removed by evaporation, the residue was then neutralized by 1N hydrochloric acid, and the mixture was extracted with ethyl acetate. The organic layer was concentrated to dryness, and the resulting solid was recrystallized from ethanol to give 295 mg of 2-(3-cyano-4-isopropoxyphenyl)-4-methyl-5-thiazolecarboxylic acid (yield: 80%).

m.p.: 220°–222° C. $^1$H-NMR (DMSO d$_6$) δ: 8.24 (d, 1H, J=2.6 Hz), 8.19 (dd, 1H, J=9.0 Hz, J=2.6 Hz), 7.38 (d, 1H, J=9.0 Hz), 4.89 (m, 1H), 2.67 (s, 3H), 1.38 (d, 6H, J=5.9 Hz).

The following compounds were prepared in the same manner as that described above.

Example 77

2-(3-Cyano-4-isobutyloxyphenyl)-4-methyl-5-thiazolecarboxylic acid was prepared from ethyl 2-(4-isobutyloxy-3-nitrophenyl)-4-methyl-5-thiazolecarboxylate (yield: 33%).

m.p.: 238°–239° C. (decomposed) $^1$H-NMR (CDCl$_3$) δ: 8.21 (d, 1H, J=2.3 Hz), 8.11 (dd, 1H, J=8.9 Hz, J=2.3 Hz), 7.03 (d, 1H, J=8.9 Hz), 3.91 (d, 2H, J=6.6 Hz ) , 2.80 (s, 3H), 2.21 (m, 1H), 1.10 (d, 6H, J=6.6 Hz).

Example 78

2-( 3-Cyano-4-neopentyloxyphenyl )-4-methyl-5-thiazolecarboxylic acid was prepared from ethyl 2-(4-neopentyloxy-3-nitrophenyl)-4-methyl-5-thiazolecarboxylate (yield: 39% ).

m.p.: 221°–236° C. $^1$H-NMR (CDCl$_3$) δ: 8.21 (d, 1H, J=2.3 Hz), 8.11 (dd, 1H, J=9.0 Hz, J=2.3 Hz), 7.02 (d, 1H, J=9.0 Hz), 3.77 (s, 2H), 2.80 (s, 3H), 1.11 (s, 9H).

Example 79

2-(3-Cyano-4-isopentyloxyphenyl)-4-methyl-5-thiazolecarboxylic acid was prepared from ethyl 2-(4-isopentyloxy-3-nitrophenyl)-4-methyl-5-thiazolecarboxylate (yield: 29%).

m.p.: 232°–234° C. $^1$H-NMR (DMSO d$_6$) δ: 8.25 (d, 1H, J=2.0 Hz), 8.20 (dd, 1H, J=8.9 Hz, J=2.0 Hz), 7.37 (d, 1H, J=8.9 Hz), 4.25 (t, 2H, J=6.5 Hz), 2.67 3H), 1.6–1.9 (m, 3H), 0.98 (d, 6H, 6.6 Hz).

Example 80

2-(3-CYano-4-(2-ethoxyethyloxy)phenyl)-4-methyl-5-thiazolecarboxylic acid was prepared from ethyl 2-(4-ethoxyethyloxy-3-nitrophenyl)-4-methyl-5-thiazolecarboxylate (yield: 23%).

m.p.: 206°–207° C. $^1$H-NMR (DMSO d$_6$) δ: 8.25 (d, 1H, J=2.0 Hz), 8.20 (dd, 1H, J=8.9 Hz, J=2.0 Hz), 7.38 (d, 1H, J=8.9 Hz), 4.36 (m, 2H), 3.78 (m, 2H), 3.56 (q, 2H, J=6.9 Hz), 2.67 (s, 3H), 1.15 (t, 3H, J=6.9 Hz).

Example 81

2-(3-Cyano-4-morpholinophenyl)-4-methyl-5-thiazolecarboxylic acid was prepared from ethyl 4-methyl-2-(4-morpholino-3-nitrophenyl)-5-thiazolecarboxylate (yield: 22%).

m.p.: 252°–255° C. $^1$H-NMR (DMSO d-6) δ: 8.12 (d, 1H, J=2.0 Hz), 8.02 (dd, 1H, J=8.9 Hz, J=2.0 Hz), 6.96 (d, 1H, J=8.9 Hz), 3.84 (m, 4H), 3.27 (m, 4H), 2.70 (s, 3H).

Example 82

2-(3-Cyano-4-piperidinophenyl)-4-methyl-5-thiazolecarboxylic acid was prepared from ethyl 4-methyl-2-(3-nitro-4-piperidinophenyl)-5-thiazolecarboxylate (yield: 28%).

m.p.: 230°–232° C. $^1$H-NMR (CDCl$_3$) δ: 8.17 (d, 1H, J=2.3 Hz), 8.03 (dd, 1H, J=8.9 Hz, J=2.3 Hz), 7.03 (d, 1H, J=8.9 Hz), 3.29 (m, 4H), 2.73 (s, 3H), 1.5–1.8 (m, 6H).

Example 83

100 mg of Ethyl 2-(3-bromo-4-isobutyloxyphenyl)-4-methyl-5-thiazolecarboxylate, 95 mg of cuprous iodide and 140 mg of sodium trifluoroacetate were suspended in 2 ml of N-methylpyrrolidone, and the mixture was heated in a nitrogen atmosphere at 140° C. for 4 hours. After completion of the reaction, the product was extracted with ethyl acetate, and the organic layer was concentrated to give a crude crystal. The resulting crystal was purified by silica gel chromatography to give 80 mg of ethyl 2-(4-isobutyloxy-3-trifluoromethylphenyl)-4-methyl-5-thiazolecarboxylate.
The product was hydrolyzed by a conventional process, following by recrystallization from hexane-ether to give 50 mg of 2-(4-isobutyloxy-3-trifluomethylphenyl)-4-methyl-5-thiazolecarboxylic acid (yield: 56%).

m.p.: 208°–211° C. $^1$H-NMR (CDCl$_3$) δ: 8.21 (d, 1H, J=2.3 Hz), 8.09 (dd, 1H, J=8.7 Hz, J=2.3 Hz), 7.03 (d, 1H, J=8.9 Hz), 3.89 (d, 2H, J=6.0 Hz), 2.80 (s, 3H), 2.1–2.3 (m, 1H), 1.07 (d, 6H, J=6.6 Hz).

Example 84

4-Methyl-2-(4-neopentyloxy-3-trifluoromethylphenyl)-5-thiazolecarboxylic acid was prepared from ethyl 2-(3-bromo-4-neopentyloxyphenyl)-4-methyl-5thiazolecarboxylate in the same manner as that described in Example 83 (yield: 48%).

m.p.: 203°–204° C. $^1$H-NMR (DMSO d-6) δ: 8.15 (m, 2H) 7.33 (d, 1H, J=8.9 Hz), 3.84 (s, 2H), 2.67 (s, 3H), 1.04 (s, 9H).

Example 85

120 mg of Ethyl 2-(3-bromo-4-neopentyloxyphenyl)-4-methyl-5-thiazolecarboxylate, 100 mg of cuprous iodide and 80 mg of lithium iodide were suspended in 2 ml of N-methyl pyrrolidone, and the suspension was heated at 150° C. for 4 hours with stirring. After completion of the reaction, the product was extracted with ethyl acetate, and the organic layer was concentrated to give a crude crystal. The resulting crystal was purified by silica gel chromatography to give 95 mg of ethyl 2-(3-iodo-4-neopentyloxyphenyl)-4-methyl-5-thiazolecarboxylate. The product was hydrolyzed by a conventional process, followed by recrystallization from hexane-ether to give 63 mg of 2-(3-iodo-4-neopentyloxyphenyl)-4-methyl-5-thiazolecarboxylic acid (yield: 58%).

m.p.: 194°–195° C. $^1$H-NMR (DMSO d-6) δ: 8.42 (d, 1H, J=2.0 Hz), 7.90 (d, 1H, J=8.9 Hz, J=2.0 Hz), 6.80 (d, 1H, J=8.9 Hz), 3.71 (s, 2H), 2.79 (s, 3H), 1.12 (s, 9H).

Example 86

150 mg of Ethyl 2-(4-isobutyloxyphenyl)-4-methyl-5-thiazolecarboxylate were dissolved in 2 ml of dichloromethane and 1.8 ml of titanium tetrachloride (1N in dichloromethane) was added thereto with cooling. Then 15 minutes after the addition, to the solution was dropwise added 0.8 ml of α,α-dichloromethyl ether, and the mixture then stirred at 0° C. for one hour, and further, allowed to react at 40° C. for 24 hours. The reaction mixture was poured into ice-water, and extracted with ethyl acetate, the organic layer was concentrated, and the resulting residue was purified by silica gel chromatography to give 60 mg of ethyl 2-(3-α,α-dichloromethyl)-4-isobutyloxyphenyl)-4-methyl-5-thiazolecarboxylate. This product was hydrolyzed by a conventional process, followed by recrystallization from hexane ether to give 45 mg of 2-(3-formyl-4-isobutyloxyphenyl)-4-methyl-5-thiazolecarboxylic acid (yield: 22%).

m.p.: 213°–217° C. $^1$H-NMR (CDCl$_3$) δ: 10.53 (s, 1H), 8.50 (br.s, 1H), 8.36 (s, 1H), 7.07 (br.s, 1H), 3.95 (d, 2H, J=5.6 Hz), 2.86 (s, 3H), 2.1–2.2 (m, 1H), 1.02 (d, 6H, J=6.6 Hz).

Examples 87–110

According to the process as described above, the following compounds were prepared:

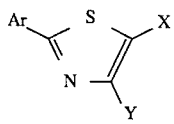

| Example No. | Ar | X | Y | Yield (%) | | $^1$H-NMR (δ in DMSO-d$_6$) and m.p. |
|---|---|---|---|---|---|---|
| 87 | 2-pyridyl | CO$_2$H | CH$_3$ | 34 | δ: | [ 8.67–8.59(m, 1H), 8.17–8.07(m, 1H), 7.94(dt, 1H, J=1.8, 7.3Hz), 7.54–7.39(m, 1H), 2.70(s, 3H) in DMSO-d$_6$ ] |
| | | | | | mp: | 200–202° C. |
| 89 | 4-pyridyl | CO$_2$H | CH$_3$ | 65 | δ: | [ 8.73(m, 2H), 7.89(m, 2H), 2.71(s, 3H) in DMSO-d$_6$ ] |
| | | | | | mp: | 200° C. (sublimed) |

| Example No. | R₁ | R₂ | X | Y | Yield (%) | ¹H-NMR (δ in CDCl₃ or DMSO-d₆) and m.p. |
|---|---|---|---|---|---|---|
| 90 | 4-F | H | CO₂H | CH₃ | 67 | δ: 8.1–7.9(m, 2H), 7.33(t, 2H, J=8.8Hz), 2.68(s, 3H) in CDCl₃ |
| 91 | 4-O–⟨4-F-C₆H₄⟩ | H | CO₂H | CH₃ | 20 | δ: 7.91(d, 2H, J=9.0Hz), 7.09–7.01(m, 4H), 6.98(d, 2H, J=9.0Hz), 2.76(s, 3H) in CDCl₃ |
| 92 | 3-Cl | 4-SO₂–⟨4-Cl-C₆H₄⟩ | CO₂H | CH₃ | 42 | δ: 8.39(d, 1H, J=2.8Hz), 8.13–7.52(m, 6H), 2.68(s, 3H) in CDCl₃<br>mp: 214–216.29 C. |
| 93 | 4-S–CH₂–⟨4-Cl-C₆H₄⟩ | H | CO₂H | CH₃ | 14 | δ: 7.9–7.2(m, 4H), 7.26(s, 4H), 4.15(s, 2H), 2.74(s, 3H) in CDCl₃ |
| 94 | 3-NO₂ | 4-NHCO–⟨2,4-diCl-C₆H₃⟩ | CO₂H | CH₃ | 62 | δ: 11.08(s, 1H), 8.52(d, 1H, J=1.6Hz), 8.32(dd, 1H, J=2.2, 8.6Hz), 7.90(dd, 1H, J=1.6, 8.6Hz), 7.78–7.63(m, 3H), 2.71(s, 3H)<br>mp: 290–291° C. |
| 95 | 3-NO₂ | 4-NHCO–⟨2,4-diOCH₃-C₆H₃⟩ | CO₂H | CH₃ | 70 | δ: 13.3br.s, 1H), 11.90(s, 1H), 8.94(d, 1H, J=8.9Hz), 8.62(d, 1H, J=2.3Hz), 8.17(dd, 1H, J=2.3, 8.9Hz), 8.01(d, 1H, J=9.6Hz), 6.70(m, 2H), 4.07(s, 3H), 3.85(s, 3H), 2.66(s, 3H)<br>mp: 285–286° C. (decomposed) |
| 96 | 4-CO–⟨thiophene⟩ | H | CO₂H | CH₃ | 23 | δ: 8.16(d, 2H, J=8.6Hz), 8.12(m, 1H), 7.94(d, 2H, J=8.6Hz), 7.90(m, 1H), 7.30(m, 1H), 2.71(s, 3H) in DMSO-d₆ |

-continued

| Example No. | R₁ | R₂ | X | Y | Yield (%) | ¹H-NMR (δ in CDCl₃ or DMSO-d₆) and m.p. |
|---|---|---|---|---|---|---|
| 97 | 4-CO-(4-Cl-C₆H₄) | H | CO₂H | CH₃ | 5 | δ: 8.09(d, 2H, J=8.0Hz), 7.85(d, 2H, J=8.3Hz), 7.76(d, 2H, J=8.7Hz), 7.49(d, 2H, J=8.3Hz), 2.71(s, 3H), in CDCl₃ |
| 98 | 4-CO-(4-F-C₆H₄) | H | CO₂H | CH₃ | 19 | δ: 8.09(d, 2H, J=8.0Hz), 7.86(d, 2H, J=7.9Hz), 7.85(d, 2H, J=8.0Hz), 7.19(dd, 2H, J=8.2, 8.7Hz), 3.0–3.7(br.s, 1H) in CDCl₃ |
| 99 | 3-CO₂Et | H | CO₂Et | CH₃ | 59 | δ: 8.57(m, 1H), 8.21–8.08(m, 2H), 7.52(t, 1H, J=7.7Hz), 4.43(q, 2H, J=7.0Hz), 4.37(q, 2H, J=7.0Hz), 2.79(s, 3H), 1.43(t, 3H, J=7.0Hz), 1.40(t, 3H, J=7.0Hz) in CDCl₃<br>mp: 70–71° C. |
| 100 | 4-CO₂Et | H | CO₂Et | CH₃ | 67 | δ: 8.18–7.95(m, 4H), 4.40(q, 2H, J=7.0Hz), 4.37(q, 2H, J=7.0Hz), 2.79(s, 3H), 1.42(t, 3H, J=7.0Hz), 1.31 (t, 3H, J=7.0Hz) in CDCl₃<br>mp: 88–89° C. |
| 101 | 4-CONH-iPr | H | CO₂H | CH₃ | 31 | δ: 8.34–8.25(m, 1H), 7.99(m, 4H), 4.14(m, 1H), 2.70(s, 3H), 1.19(d, 6H, J=6.6Hz) in DMSO-d₆<br>mp: 225–226° C. (decomposed) |
| 102 | 4-CONH-(2,4-diMe-C₆H₃) | H | CO₂H | CH₃ | 35 | δ: 9.90(s, 1H), 8.10(s, 4H), 7.26–7.07(m, 3H), 2.71(s, 3H), 2.30(s, 3H), 2.21(s, 3H) in DMSO-d₆<br>mp: 248–249° C. (decomposed) |
| 103 | 4-CONH-(3,4-diOMe-C₆H₃) | H | CO₂H | CH₃ | 36 | δ: 9.49(s, 1H), 8.08(s, 4H), 7.53(d, 1H, J=8.6Hz), 6.68–6.51(m, 2H), 3.82(s, 3H), 3.79(s, 3H), 2.71(s, 3H) in DMSO-d₆<br>mp: 234–235° C. (decomposed) |

-continued

| Example No. | R₁ | R₂ | X | Y | Yield (%) | ¹H-NMR (δ in CDCl₃ or DMSO-d₆) and m.p. |
|---|---|---|---|---|---|---|
| 104 | 4-CONH-(4-pyridyl) | H | $CO_2H$ | $CH_3$ | 11 | δ: [8.42–8.36(m, 1H), 8.27–8.05(m, 5H), 7.95–7.75(m, 1H), 7.27–7.12(m, 1H), 2.71(s, 3H) in DMSO-d₆] mp: 285–287° C. (decomposed) |
| 105 | 3-CF₃ | H | $CO_2Et$ | $CH_3$ | 51 | δ: [8.24–8.07(m, 2H), 7.77–7.56(m, 2H), 4.37(q, 2H, J=7.0Hz), 1.40(t, 3H, J=7.0Hz) in DMSO-d₆] mp: 87–88° C. |
| 106 | 4-CO-phenyl | H | $CONH_2$ | $CH_3$ | 37 | δ: [7.6–8.2(m, 11H), 2.66(s, 3H) in CDCl₃] |
| 107 | 4-CF₃ | H | H | $CO_2H$ | 42 | δ: [8.21–8.09(m, 3H), 7.71(d, 2H, J=8.1Hz), in CDCl₃] mp: 190° C. (sublimed) |
| 108 | 3-CF₃ | H | H | $CO_2H$ | 58 | δ: [8.27–8.08(m, 3H), 7.79–7.49(m, 2H) in CDCl₃] mp: 198–200° C. |
| 109 | 3-NO₂ | H | H | $CO_2H$ | 80 | δ: [13.25(brs, 1H), 8.73(dd, 1H, J=1.6, 2.3Hz), 8.60(s, 1H), 8.42–8.34(m, 2H), 7.84(dd, 1H, J=7.9, 8.2Hz) in DMSO-d₆] mp: 221–222° C. |
| 110 | 4-CO-phenyl | H | H | $CO_2H$ | 35 | δ: [8.50(s, 1H), 8.15–7.70(m, 9H) in CDCl₃] |

Pharmacological Test 1 (In Vitro Determination)

(1) Preparation of test compounds:

Test compounds (compounds of Ex. No. listed in Table 1) were dissolved in dimethylsulfoxide and diluted with a 50 mM phosphate buffer to prepare aqueous solutions respectively having predetermined concentrations.

(2) Determining method:

45 nmol of xanthine and test compounds prepared so as to have various concentrations were added to 3 ml of a phosphate buffer having a pH value of 7.4 and containing 3 mU of xanthine oxidase (derived from a butter milk; available from Sigma Chemical Company). A reaction was allowed to proceed at 37° C., and the change in OD at 292 nm based on the formation of uric acid was measured with time through the use of a spectrophotometer U-3200 (manufactured by Hitachi, Limited) to determine the initial reaction rate. The inhibition rate was determined by the following equation:

$$\text{Inhibition (\%)} = \frac{\text{(initial rate of control)} - \text{(initial rate in the case where inhibitor was added)}}{\text{(initial rate of control)}} \times 100$$

The inhibition (%) was determined on each test compound prepared according to (1), and the $IC_{50}$ value on the xanthine oxidase (XOD) inhibition was calculated from the value of inhibition. The results are given in Table 1.

TABLE 1

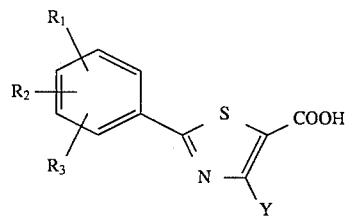

| Example No. | $R_1$ | $R_2$ | $R_3$ | Y | $IC_{50}$ (M) |
|---|---|---|---|---|---|
| Control | | allopurinol | | | $1.6 \times 10^{-6}$ |
| 1 | 3-O-iso-Pr | H | H | $CH_3$ | $6.7 \times 10^{-8}$ |
| 2 | 4-O-iso-Pr | H | H | $CH_3$ | $2.8 \times 10^{-8}$ |
| 3 | 3-$NO_2$ | H | H | $CH_3$ | $1.4 \times 10^{-8}$ |
| 4 | 4-$NO_2$ | H | H | $CH_3$ | $9.0 \times 10^{-7}$ |
| 5 | 3-$CF_3$ | H | H | $CH_3$ | $6.3 \times 10^{-10}$ |
| 6 | 4-$CF_3$ | H | H | $CH_3$ | $3.1 \times 10^{-7}$ |
| 7 | 4-$OCH_2$-cyclohexyl | H | H | $CH_3$ | $4.6 \times 10^{-8}$ |
| 8 | 4-$O(CH_2)_3$-cyclohexyl | H | H | $CH_3$ | $3.2 \times 10^{-9}$ |
| 9 | 4-$OCH_2$-C$_6$H$_4$-Cl | H | H | $CH_3$ | $1.7 \times 10^{-8}$ |
| 10 | 4-$OCH_2$-C$_6$H$_4$-F | H | H | $CH_3$ | $3.1 \times 10^{-8}$ |
| 11 | 4-$OCH_2COOH$ | H | H | $CH_3$ | $7.7 \times 10^{-8}$ |
| 12 | 4-$O(CH_2)_4COOH$ | H | H | $CH_3$ | $1.2 \times 10^{-8}$ |
| 13 | 3-COOH | H | H | $CH_3$ | $3.2 \times 10^{-7}$ |
| 14 | 4-COOH | H | H | $CH_3$ | $3.2 \times 10^{-9}$ |
| 15 | 3-CONH-C$_6$H$_4$-Cl | H | H | $CH_3$ | $1.5 \times 10^{-7}$ |
| 16 | 4-CONH-C$_6$H$_4$-Cl | H | H | $CH_3$ | $3.8 \times 10^{-10}$ |

TABLE 1-continued

| Example No. | R₁ | R₂ | R₃ | Y | IC₅₀ (M) |
|---|---|---|---|---|---|
| 17 | 4-CON(CH₃)—⟨C₆H₄⟩—Cl | H | H | CH₃ | $5.0 \times 10^{-7}$ |
| 18 | 4-N(CH₃)₂ | H | H | CH₃ | $4.3 \times 10^{-8}$ |
| 19 | 3-CO—⟨C₆H₅⟩ | H | H | CH₃ | $1.2 \times 10^{-8}$ |
| 20 | 4-CO—⟨C₆H₅⟩ | H | H | CH₃ | $6.0 \times 10^{-9}$ |
| 21 | 3-Cl | H | H | OH | $7.2 \times 10^{-7}$ |
| 22 | 4-O-iso-Pr | H | H | OH | $4.5 \times 10^{-8}$ |
| 23 | 4-O-iso-Pr | H | H | OCH₃ | $1.3 \times 10^{-7}$ |
| 24 | 2-Cl | 5-NO₂ | H | CH₃ | $6.7 \times 10^{-8}$ |
| 25 | 3-Ac | 4-OH | H | CH₃ | $3.0 \times 10^{-7}$ |
| 26 | 3-CF₃ | 5-CF₃ | H | CH₃ | $5.7 \times 10^{-9}$ |
| 27 | 3-Cl | 5-Cl | H | CH₃ | $1.0 \times 10^{-8}$ |
| 28 | 3-Cl | 4-OH | 5-Cl | CH₃ | $2.6 \times 10^{-8}$ |
| 29 | 3-tert-Bu | 4-OH | 5-tert-Bu | CH₃ | $6.5 \times 10^{-8}$ |
| 30 | 3-CH₃ | 4-OH | 5-CH₃ | CH₃ | $4.2 \times 10^{-8}$ |
| 31 | 3-NO₂ | 4-O-iso-Pr | H | CH₃ | $5.7 \times 10^{-10}$ |
| 32 | 3-NO₂ | 4-OCH₂—⟨cyclohexyl⟩ | H | CH₃ | $1.8 \times 10^{-10}$ |
| 33 | 3-NO₂ | 4-OEt | H | CH₃ | $3.6 \times 10^{-10}$ |
| 34 | 3-NO₂ | 4-O-iso-Bu | H | CH₃ | $2.4 \times 10^{-9}$ |
| 35 | 3-NO₂ | 4-S-iso-Pr | H | CH₃ | $3.0 \times 10^{-10}$ |
| 36 | 3-NO₂ | 4-S—⟨C₆H₄⟩—Cl | H | CH₃ | $2.0 \times 10^{-11}$ |
| 37 | 3-NO₂ | 4-NEt₂ | H | CH₃ | $1.8 \times 10^{-9}$ |
| 38 | 3-NO₂ | 4-N⟨piperidinyl⟩ | H | CH₃ | $1.8 \times 10^{-9}$ |
| 39 | 3-NO₂ | 4-O(CH₂)₂OEt | H | CH₃ | $2.9 \times 10^{-9}$ |
| 40 | 3-NO₂ | 4-O-CH₂CH₂CH(CH₃)₂ | H | CH₃ | $6.7 \times 10^{-10}$ |
| 41 | 3-NO₂ | 4-O(CH₂)₅CH₃ | H | CH₃ | $3.2 \times 10^{-10}$ |
| 42 | 3-NO₂ | 4-O-CH(CH₂CH₃)₂ | H | CH₃ | $2.0 \times 10^{-9}$ |

TABLE 1-continued

[Structure: substituted phenyl (R1, R2, R3) attached to a thiazole ring bearing S, N, COOH and Y substituents]

| Example No. | R$_1$ | R$_2$ | R$_3$ | Y | IC$_{50}$ (M) |
|---|---|---|---|---|---|
| 43 | 3-NO$_2$ | 4-O-CH$_2$-C(CH$_3$)$_3$ (neopentyloxy) | H | CH$_3$ | $6.4 \times 10^{-10}$ |
| 44 | 3-NO$_2$ | 4-N-piperidinyl | H | CH$_3$ | $1.6 \times 10^{-9}$ |
| 45 | 3-NO$_2$ | 4-N-morpholinyl | H | CH$_3$ | $1.8 \times 10^{-9}$ |
| 46 | 3-NO$_2$ | 4-(4-methylpiperazin-1-yl) | H | CH$_3$ | $2.4 \times 10^{-9}$ |
| 49 | 3-Cl | 4-OEt | H | CH$_3$ | $2.3 \times 10^{-9}$ |
| 50 | 3-Cl | 4-O-isoPr | H | CH$_3$ | $2.4 \times 10^{-9}$ |
| 51 | 3-Cl | 4-S-isoBu | H | CH$_3$ | $2.1 \times 10^{-9}$ |
| 52 | 3-Cl | 4-O-CH$_2$CH$_2$CH(CH$_3$)$_2$ (isoamyloxy) | H | CH$_3$ | $2.7 \times 10^{-9}$ |
| 53 | 3-Cl | 4-O-CH$_2$CH(Et)$_2$ (2-ethylbutyloxy) | H | CH$_3$ | $2.7 \times 10^{-9}$ |
| 54 | 3-Cl | 4-O-CH$_2$-C(CH$_3$)$_3$ (neopentyloxy) | H | CH$_3$ | $2.9 \times 10^{-9}$ |
| 55 | 3-Cl | 4-O(CH$_2$)$_2$OEt | H | CH$_3$ | $7.0 \times 10^{-9}$ |
| 56 | 3-Cl | 4-O-CH$_2$CH$_2$-(morpholin-4-yl) | H | CH$_3$ | $1.5 \times 10^{-9}$ |
| 57 | 3-Cl | 4-O-CH$_2$CH$_2$-(piperidin-1-yl) | H | CH$_3$ | $1.2 \times 10^{-9}$ |
| 58 | 3-Cl | 4-OCH$_2$-(4-fluorophenyl) | H | CH$_3$ | $3.4 \times 10^{-9}$ |
| 59 | 3-Cl | 4-N-morpholinyl | H | CH$_3$ | $3.8 \times 10^{-10}$ |
| 60 | 3-Cl | 4-N-piperidinyl | H | CH$_3$ | $2.4 \times 10^{-10}$ |

TABLE 1-continued

[Structure: phenyl ring with R1, R2, R3 substituents attached to a thiazole ring bearing COOH and Y substituents]

| Example No. | R₁ | R₂ | R₃ | Y | IC₅₀ (M) |
|---|---|---|---|---|---|
| 61 | 3-Cl | 4-S-(C₆H₄)-Cl (4-chlorophenylthio) | H | CH₃ | $2.0 \times 10^{-9}$ |
| 62 | 3-Cl | 4-SO-(C₆H₄)-Cl (4-chlorophenylsulfinyl) | H | CH₃ | $6.4 \times 10^{-10}$ |
| 63 | 3-Br | 4-O-isoBu | H | CH₃ | $9.4 \times 10^{-10}$ |
| 64 | 3-Br | 4-O(CH₂)₂OEt | H | CH₃ | $2.9 \times 10^{-9}$ |
| 65 | 3-Br | 4-S-(C₆H₄)-Cl (4-chlorophenylthio) | H | CH₃ | $1.6 \times 10^{-9}$ |
| 66 | 3-Br | 4-N-piperidinyl | H | CH₃ | $6.3 \times 10^{-10}$ |
| 67 | 3-F | 4-O-isoBu | H | CH₃ | $1.5 \times 10^{-9}$ |
| 68 | 3-Cl | 4-O-isoPr | 5-Cl | CH₃ | $.2.2 \times 10^{-9}$ |
| 69 | 3-Cl | 4-O-isoBu | 5-Cl | CH₃ | $1.5 \times 10^{-9}$ |
| 70 | 3-Cl | 4-O-CH₂CH(Et)₂ (2-ethylbutoxy) | 5-Cl | CH₃ | $8.0 \times 10^{-10}$ |
| 71 | 3-Cl | 4-O-CH₂CH₂CH(CH₃)₂ (isopentyloxy) | 5-Cl | CH₃ | $1.5 \times 10^{-9}$ |
| 72 | 3-Cl | 4-O-CH₂CH₂-(morpholinyl) | 5-Cl | CH₃ | $7.0 \times 10^{-10}$ |
| 73 | 4-CO-(C₆H₅) (benzoyl) | H | H | CH₃ | $6.2 \times 10^{-9}$ |
| 74 | 4-CO-(C₆H₄)-4-Me (4-methylbenzoyl) | H | H | CH₃ | $4.8 \times 10^{-9}$ |
| 75 | 4-CO-(2-Me,4-Me-C₆H₃) (2,4-dimethylbenzoyl) | H | H | CH₃ | $8.3 \times 10^{-10}$ |
| 76 | 3-CN | 4-O-isoPr | H | CH₃ | $9.3 \times 10^{-10}$ |
| 77 | 3-CN | 4-O-isoBu | H | CH₃ | $1.8 \times 10^{-9}$ |

TABLE 1-continued

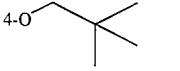

| Example No. | R₁ | R₂ | R₃ | Y | IC$_{50}$ (M) |
|---|---|---|---|---|---|
| 78 | 3-CN | 4-O-neopentyl | H | CH$_3$ | $1.9 \times 10^{-9}$ |
| 79 | 3-CN | 4-O-isopentyl | H | CH$_3$ | $2.2 \times 10^{-9}$ |
| 80 | 3-CN | 4-O(CH$_2$)$_2$OEt | H | CH$_3$ | $1.9 \times 10^{-9}$ |
| 81 | 3-CN | 4-N-morpholino | H | CH$_3$ | $1.7 \times 10^{-9}$ |
| 82 | 3-CN | 4-N-piperidino | H | CH$_3$ | $2.7 \times 10^{-9}$ |
| 83 | 3-CF$_3$ | 4-O-isoBu | H | CH$_3$ | $1.1 \times 10^{-9}$ |
| 84 | 3-CF$_3$ | 4-O-neopentyl | H | CH$_3$ | $2.9 \times 10^{-9}$ |
| 85 | 3-I | 4-O-neopentyl | H | CH$_3$ | $1.2 \times 10^{-10}$ |
| 86 | 3-CHO | 4-O-isoBu | H | CH$_3$ | $5.1 \times 10^{-10}$ |

Pharmacological Test 2 (Determination of Oral Administration)

Test compounds suspended in a 5% gum arabic solution was forcibly administered by oral administration (compounds of Ex. No. of Table 2, dose: 1 mg/kg) to ICR male mice (age: about 7 weeks) (one group: 6 mice) by means of an oral probe. 2 hours after the administration, thoracotomy was conducted under etherization to collect blood from the heart, and serum was removed by a conventional process. The serum uric acid was measured by a biochemical automatic analyzer (Flexigem; Electro-Nucleonics, Inc.) by using a uric acid measurement kit (UA reagent; International Reagent) to determine the percentage of the lowering of uric acid.

$$\text{Lowering in uric acid (\%)} = \frac{\text{(uric acid level of control animal)} - \text{(uric acid level of test-compound-administration animal)}}{\text{uric acid level of object animal}} \times 100$$

The results are given in Table 2.

TABLE 2

| Example No. | Activity of lowering uric acid (%) | Example No. | Activity of lowering uric acid (%) |
|---|---|---|---|
| allopurinol | 73 | 33 | 71 |
| 5 | 37 | 34 | 76 |
| 8 | 28 | 35 | 57 |
| 16 | 21 | 36 | 14 |
| 18 | 22 | 37 | 74 |
| 20 | 18 | 38 | 91 |
| 26 | 63 | 39 | 82 |
| 31 | 90 | 40 | 85 |
| 32 | 48 | 41 | 92 |
| 42 | 75 | 59 | 62 |
| 43 | 85 | 60 | 55 |
| 44 | 83 | 61 | 32 |
| 45 | 88 | 62 | 35 |
| 46 | 75 | 63 | 35 |
| 47 | 92 | 64 | 25 |
| 48 | 88 | 65 | 42 |
| 49 | 35 | 66 | 65 |
| 50 | 20 | 67 | 50 |
| 51 | 78 | 68 | 13 |
| 52 | 47 | 69 | 55 |
| 53 | 29 | 70 | 15 |
| 54 | 12 | 71 | 50 |
| 55 | 45 | 72 | 48 |

TABLE 2-continued

| Example No. | Activity of lowering uric acid (%) | Example No. | Activity of lowering uric acid (%) |
| --- | --- | --- | --- |
| 56 | 50 | 73 | 18 |
| 57 | 15 | 74 | 39 |
| 58 | 18 | 75 | 33 |
| 76 | 86 | 82 | 93 |
| 77 | 95 | 83 | 86 |
| 78 | 91 | 84 | 80 |
| 79 | 89 | 85 | 77 |
| 80 | 87 | 86 | 72 |
| 81 | 91 | | |

No. 47

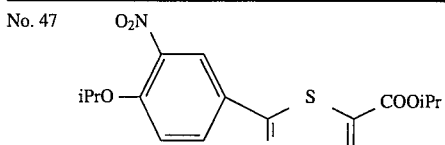

No. 48

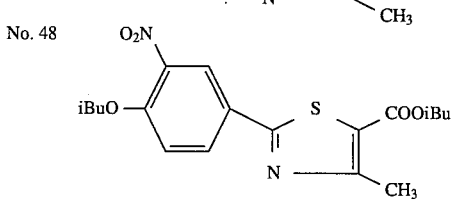

Pharmacological Test 3 (Interleukin 1 Production Inhibitory Activity)

1 ml of a 5% oyster glycogen solution was intra-abdominally administered to a BALB/c mouse (male, 8 weeks in age), and 4 days after the administration, the infiltrated abdominal exuded cells were adhered to a plastic dish for 2 hours, and 1 μg/ml of LPS was allowed to act on macrophage ($1 \times 10^6$ cells). Interleukin 1 extricated on the supernatant in 24 hours was measured by an ELISA technique. The test compound (compounds of Ex. No. described in Table 3) was prepared so as to have a concentration of $10^{-6}$M, and the interleukin 1 production inhibitory activity was, expressed in terms of the percentage inhibition based on the amount of production of the control. The results are given in Table 3.

TABLE 3

| Example No. | Interleukin 1 production inhibitory activity (%) |
| --- | --- |
| 1 | 83 |
| 5 | 60 |
| 6 | 38 |
| 7 | 39 |
| 11 | 23 |
| 12 | 42 |
| 14 | 35 |
| 15 | 38 |
| 20 | 65 |
| 22 | 45 |
| 26 | 57 |
| 27 | 43 |
| 28 | 52 |
| 40 | 36 |
| 43 | 39 |
| 44 | 22 |
| 45 | 18 |
| 49 | 48 |
| 50 | 42 |
| 52 | 33 |
| 58 | 19 |
| 64 | 28 |

TABLE 3-continued

| Example No. | Interleukin 1 production inhibitory activity (%) |
| --- | --- |
| 67 | 48 |
| 73 | 65 |
| 74 | 52 |
| 75 | 48 |

Pharmacological Test 4 (Collagen Arthritis Inhibitory Activity)

An emulsion comprising a bovine II type collagen and incomplete Freund's adjuvant in a proportion of 1:1 were intradermally injected to Lewis rats (male, about 6 weeks in age) (one group: 8 mice) at the region of the back so that the amount of antigen was 2 mg/rat, thereby inducing arthritis. The compound of Ex. No. 35 was suspended in a 5% gum arabic solution, and orally administered 5 times per week in two groups of 10 mg/kg and 50 mg/kg from the sensitized day. Only the gum arabic solution was administered to the control. Then 6 weeks after the sensitization, the percentage increase in the volume of the right foot was measured and expressed in terms of the percentage swelling, and the anti-collagen antibody titer of the serum was measured by the ELISA technique. The results are given in Table 4.

As can be seen from Table 5, the compound of the present invention inhibited the swelling of foot-pad depending upon the dose when administered in doses of 100 mg/kg and 50 mg/kg (the percentage inhibitions were respectively 44.1% and 53.4%). Further, the compound of the present invention exhibited a tendency to inhibit the antibody titer of serum anti-collagen involved in the sideration of collagen arthritis in a group of administration in doses of 10 mg/kg and 50 mg/kg. The above-described facts suggest that there is a possibility that the compound of the present invention has an anti-arthritic activity and an anti-collagen-antibody is involved in one of the action mechanisms.

TABLE 4

| | Dose (mg/kg) | Swelling (%) | Antibody titer of anti-collagen (μU/ml) |
| --- | --- | --- | --- |
| control | | 45.5 ± 5.1 | 2.04 ± 0.36 |
| compound of | 10 | 25.4 ± 5.3* | 1.88 ± 0.20 |
| Ex. No. 73 | 50 | 21.2 ± 4.2** | 1.68 ± 0.32 |

Note)
*$P < 0.05$
**$P < 0.01$

Pharmaceutical Preparation Example 1
Tablets wherein one tablet had the following composition were prepared.

| | |
| --- | --- |
| Compound prepared in Ex. 31 | 50 mg |
| Lactose | 230 mg |
| Potato starch | 80 mg |
| Polyvinyl pyrrolidone | 11 mg |
| Magnesium stearate | 5 mg |
| | 376 mg |

The compound of the above-described Example, lactose and potato starch were mixed with each other, and a 20% ethanol solution of polyvinyl pyrrolidone was evenly infiltrated into the mixture, passed through a 20 nm mesh sieve, dried at 45° C., and again passed through a 15 nm mesh sieve. The granules thus prepared were mixed with magnesium stearate, and the mixture was compressed into a tablet.

Pharmaceutical Preparation Example 2

The pharmaceutical preparation example 2 was repeated, except that the compound prepared in Ex. 69 was used instead of that in Ex. 31.

[Industrial Applicability]

In accordance with the present invention, pharmaceutical compositions containing a 2-arylthiazole derivative or a pharmaceutically acceptable salt thereof, which is efficacious for a treatment of gout or hyperuricemia, are provided. Accordingly, the present invention is applicable to the manufacture of pharmaceutical compositions.

We claim:

1. A 2-arylthiazole derivative having the following formula (I), and a pharmaceutically acceptable salt thereof:

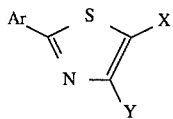

wherein Ar is an unsubstituted or substituted furyl group; or a group represented by the following formula (II):

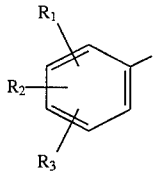

wherein $R_1$, $R_2$, and $R_3$ are hydrogen, a halogen atom, or a nitro, cyano or formyl group; or a group of OR, $S(O)_nR$ and $NRR^1$ (wherein n is an integer of from 1 to 2, R represents an unsubstituted or substituted $C_{1-10}$ alkyl, aryl, aralkyl, alkylcarbonyl, arylcarbonyl or aralkylcarbonyl group, $R^1$ represents a hydrogen atom, or an unsubstituted or substituted $C_{1-10}$ alkyl, aryl, aralkyl, alkylcarbonyl, arylcarbonyl or aralkylcarbonyl group; or R and $R^1$, taken together with the nitrogen atom bonded thereto, represent atoms forming an unsubstituted or substituted 5- or 7-membered heterocyclic ring), or a group of COR" wherein R" represents an unsubstituted or substituted $C_{1-10}$ alkyl, aryl or aralkyl group; a hydroxyl group; an unsubstituted or substituted $C_{1-10}$ alkoxy, aryloxy or aralkyloxy group; an amino group; or an unsubstituted or substituted $C_{1-10}$ alkyl (mono- or di-substituted, independently) amino, aryl (mono- or di-substituted, independently) amino or aralkyl (mono- or di-substituted, independently) amino group, or a 5- to 7-membered cyclic amino group, and at least one of $R_1$, $R_2$ or $R_3$ is other than hydrogen;

X is a hydrogen atom, or a $C_{1-14}$ alkyl, carboxyl, $C_{1-5}$ alkoxycarbonyl, carbamoyl or $C_{1-4}$ alkyl (mono- or di-substituted) aminocarbonyl group; and Y represents a hydrogen atom or a $C_{1-4}$ alkyl, carboxyl, $C_{1-5}$ alkoxycarbonyl, carbamoyl or $C_{1-4}$ alkyl (mono- or di-substituted) aminocarbonyl group, with the proviso that when at least one group of $R_1$, $R_2$ and $R_3$ represents a halogen atom, or an alkoxy, alkylamino or nitro group, at least one group of the two other groups represents a group other than a hydrogen atom; when at least one group of $R_1$, $R_2$ and $R_3$ is a halogen atom and another group is a hydrogen atom, a remaining group is a group other than a halogen atom, or an alkoxy, alkylamino or acylamino group, with the additional proviso that when any one of $R_1$, $R_2$ or $R_3$ is OR, one of the remaining groups cannot represent hydrogen while the other group represents OR, or the remaining two groups cannot both represent OR at the same time, nor do all of $R_1$–$R_3$ represent halogen; with the further proviso that both X and Y do not represent carboxyl, $C_{1-5}$ alkoxycarbonyl, carbamoyl or $C_{1-4}$ alkyl (a mono- or di-substituted) aminocarbonyl group at the same time.

2. A 2-arylthiazole derivative of the formula (I) and a pharmaceutically acceptable salt thereof in accordance with claim 1 wherein Ar represents a group of the formula (II), and $R_1$ is a halogen atom, or a nitro, cyano or formyl group, $R_2$ is a member of the group consisting of OR, $S(O)_nR$ and NRR' wherein n is an integer of from 0 to 2, R represents an unsubstituted or substituted $C_{1-10}$ alkyl, aryl, aralkyl, alkylcarbonyl, arylcarbonyl or aralkylcarbonyl group, $R^1$ represents a hydrogen atom, or an unsubstituted or substituted $C_{1-10}$ alkyl, aryl, aralkyl, alkylcarbonyl, arylcarbonyl or aralkylcarbonyl group; or R and $R^1$ taken together with the nitrogen atom bonded thereto, represent atoms forming an unsubstituted or substituted 5- to 7-membered heterocyclic ring), and $R_3$ represents a hydrogen or halogen atom.

3. A 2-arylthiazole derivative and a pharmaceutically acceptable salt thereof in accordance with claim 2, wherein X is a carboxyl, $C_{1-5}$ alkoxy-carbonyl, carbamoyl or $C_{1-4}$ alkyl (mono- or di-substituted) aminocarbonyl group; and Y is a hydrogen atom, or a $C_{1-4}$ alkyl group.

4. A 2-arylthiazole derivative of the formula (I) and a pharmaceutically acceptable salt thereof, in accordance with claim 1, wherein Ar represents a group of the formula (II), and $R_1$ represents an m-nitro or m-cyano group, $R_2$ represents a member of the group consisting of OR, $S(O)_nR$ and NRR' wherein n is an integer of from 0 to 2, R represents an unsubstituted or substituted alkyl, aryl, aralkyl, alkylcarbonyl, arylcarbonyl or aralkylcarbonyl group, R' represents a hydrogen atom, or an unsubstituted or substituted $C_{1-10}$ alkyl, aryl, aralkyl, alkylcarbonyl, arylcarbonyl or aralkylcarbonyl group; or R and R', taken together with the nitrogen atom bonded thereto, represent atoms forming an unsubstituted or substituted 5- to 7-membered heteroxyclic ring, and $R_3$ represents a hydrogen atom;

X represents a carboxyl, $C_{1-5}$ alkoxycarbonyl, carbamoyl or $C_{1-4}$ alkyl (mono-or di-substituted aminocarbonyl group; and Y represents a hydrogen atom, or a $C_{1-4}$ alkyl group.

5. A 2-arylthiazole derivative of the formula (I) and a pharmaceutically acceptable salt thereof in accordance with claim 1 wherein Ar represents a group of the formula (II), and $R^1$ represents an m-halogen atom, $R_2$ represents a member of the group consisting of OR, $S(O)_nR$ and NRR' wherein n is an integer of from 0 to 2, R represents an unsubstituted or substituted $C_{1-10}$ alkyl, aryl, aralkyl, alkylcarbonyl, arylcarbonyl or aralkylcarbonyl group, R' represents a hydrogen atom, or an unsubstituted or substituted $C_{1-10}$ alkyl, aryl, aralkyl, alkylcarbonyl, arylcarbonyl or aralkylcarbonyl group; or R and R', taken together with the nitrogen atom bonded thereto, represent atoms forming an unsubstituted or substituted 5-to 7-membered heterocyclic ring, and $R_3$ represents a hydrogen or halogen atom.

6. A 2-arylthiazole derivative of the formula (I) and a pharmaceutically acceptable salt thereof in accordance with claim 1, wherein Ar represents a group of the formula (II), and $R_1$ represents an m-halogen atom, $R_2$ represents a group of OR, $S(O)_nR$ and NRR' wherein n is an integer of from 0 to 2, R represents an unsubstituted or substituted $C_{1-10}$ alkyl, aryl, aralkyl, alkylcarbonyl, arylcarbonyl or aralkylcarbonyl group, R' represents a hydrogen atom, or an unsubstituted or substituted $C_{1-10}$ alkyl, aryl, aralkyl, alkylcarbonyl, arylcarbonyl or aralkylcarbonyl group; or R and R', taken together with the nitrogen atom bonded thereto, represent atoms forming an unsubstituted or substituted 5- to 7-membered heterocyclic ring, and $R_3$ represents a hydrogen or halogen atom;

X represents a carboxyl, $C_{1-5}$ alkoxycarbonyl, carbamoyl or $C_{1-4}$ alkyl (mono- or di-substituted)-aminocarbonyl group; and Y represents a $C_{1-4}$ alkyl group.

7. A 2-arylthiazole derivative of the following formula (I-a) and a pharmaceutically acceptable salt thereof in accordance with claim 1:

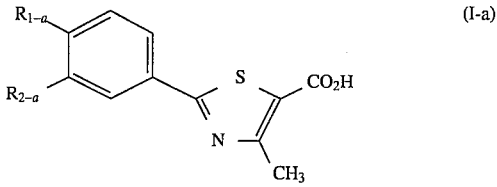

wherein $R_{1-a}$ is a $C_{2-8}$, alkoxy group and $R_{2-a}$ is a nitro group;

$R_{1-a}$ is a morpholino, 4-N-methylpiperazine-1-yl or piperidino group and $R_{2-a}$ is a nitro group;

$R_{1-a}$ is a morpholino, 4-N-methylpiperazine-1-yl or piperidino group and $R_{2-a}$ is a cyano group;

$R_{1-a}$ is a $C_{2-8}$ alkoxy group and $R_{2-a}$ is a cyano group; or $R_{1-a}$ is an unsubstituted benzoyl group or a benzoyl group substituted by one or two groups selected from the group consisting of a methyl group, chlorine atom or methoxy group, and $R_{2-a}$ is a hydrogen atom.

8. An 2-arylthiazole derivative of the following formula (I-b) and a pharmaceutically acceptable salt thereof in accordance with claim 2:

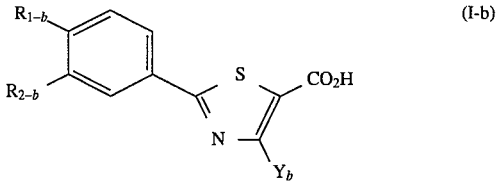

wherein $R_{1-b}$ is OR or SR group wherein R represents a $C_{2-8}$ alkyl, morpholino, 4-N-methyl piperazine-1-yl or piperidino group;

$R_{2-b}$ represents a nitro, trifluoromethyl or cyano group, and $Y_b$ represents a hydrogen atom or a methyl group; or $R_{1-b}$ represents a group of the formula

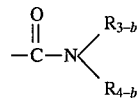

wherein $R_{3-b}$ represents an unsubstituted or substituted phenyl group and $R_{4-b}$ represents a hydroen atom or a methyl group.

9. The 2-arylthiazole derivative of claim 1 wherein when X represents a carboxyl group, Y represents a hydrogen atom or a $C_{1-4}$ alkyl group.

10. A 2-arylthiazole derivative having the following formula (I), and a pharmaceutically acceptable salt thereof:

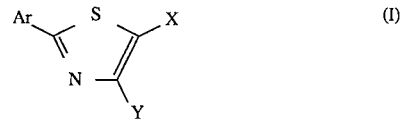

wherein Ar represents a group of the formula (II)

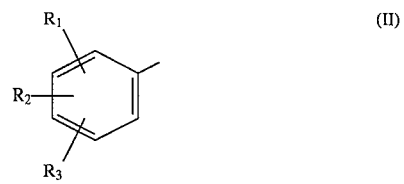

wherein $R_1$ represents COR" wherein R" represents an unsubstituted or substituted $C_{1-10}$ alkyl, aryl or aralkyl group; wherein at least one member of the group of $R_2$ and $R_3$ is a hydrogen, a halogen atom, or a nitro, cyano or formyl group; or a member selected from the group consisting of OR, $S(O)_n R$ and $NRR^1$ wherein n is an integer of 1 to 2, R represents an unsubstituted or substituted $C_{1-10}$ alkyl, aryl, aralkyl, alkylcarbonyl, arylcarbonyl or aralkylcarbonyl group, $R^1$ represents a hydrogen atom, or an unsubstituted or substituted $C_{1-10}$ alkyl, aryl, aralkyl, alkylcarbonyl, arylcarbonyl or aralkylcarbonyl group; or R and $R^1$ taken together with the nitrogen atom bonded thereto, represent atoms forming an unsubstituted or substituted 5- to 7-membered heterocyclic ring or COR" wherein R" represents an unsubstituted or substituted $C_{1-10}$ alkyl, aryl or aralkyl group; a hydroxyl group; an unsubstituted or substituted $C_{1-10}$ alkoxy, aryloxy or aralkyloxy group; an amino group; or an unsubstituted or substituted $C_{1-10}$ alkyl (mono- or disubstituted) amino, aryl (mono- or di-substituted) amino or aralkyl (mono-or di-substituted) amino group, or a 5- to 7-membered cyclic amino group; X represents a carboxyl, $C^{1-5}$ alkoxycarbonyl carbamoyl or $C_{1-4}$ alkyl (mono- or di-substituted) aminocarbonyl group; and y represents a hydrogen atom, or a $C_{1-4}$ alkyl group.

11. A pharmaceutical composition comprising an effective amount of the 2-arylthiazole derivative of claim 1.

12. A pharmaceutical composition in accordance with claim 11 wherein Ar is a group of the formula (II), and at least one group of $R_1$, $R_2$ and $R_3$ is a halogen atom, or a nitro, cyano or formyl group; or a group of OR, $S(O)_n R$ or NRR' (wherein n is an integer of from 0 to 2, R is an unsubstituted or substituted $C_{1-10}$ alkyl, aryl, aralkyl, alkylcarbonyl, arylcarbonyl or aralkylcarbonyl group, and R' is a hydrogen atom, or an unsubstituted or substituted $C_{1-10}$ alkyl, aryl, aralkyl, alkylcarbonyl, arylcarbonyl or aralkylcarbonyl group; or R and R' taken together with the nitrogen atom bonded thereto, are atoms forming an unsubstituted or substituted 5- to 7- membered heterocylic ring), or a group of COR" (wherein R" is an unsubstituted or substituted $C_{1-10}$ alkyl, aryl or aralkyl group, a hydroxyl group, an unsubstituted or substituted $C_{1-10}$ alkoxy, aryloxy or aralkyloxy group, an amino group, or an unsubstituted or substituted $C_{1-10}$ alkyl (mono- or di-substituted, independently) amino, aryl (mono- or di-substituted, independently) amino or aralky (mono- or di-substituted, independently) amino group, or a 5- to 7- membered cyclic amino group);

X is a carboxyl, $C_{1-5}$ alkoxycarbonyl, carbamoyl or $C_{1-4}$ alkyl (mono- or di-substituted) aminocarbonyl group.

13. The pharmaceutical composition of claim 11 wherein when X represents a carboxyl group, Y represents a hydrogen atom or a $C_{1-4}$ alkyl group.

14. A pharmaceutical composition comprising an effective amount of the 2-arylthiazole derivative of claim 10.

15. A method for treating a patient afflicted with gout or hyperuricemia which comprises administering to said patient a uric acid-lowering effective amount of the pharmaceutical composition of claim 11.

* * * * *

UNITED STATES PATENT AND TRADEMARK OFFICE
CERTIFICATE OF CORRECTION

PATENT NO.        : 5,614,520
APPLICATION NO.   : 08/380214
DATED             : March 25, 1997
INVENTOR(S)       : Shiro Kondo et al.

Page 1 of 1

It is certified that error appears in the above-identified patent and that said Letters Patent is hereby corrected as shown below:

Claim 1: Column 47, line 38, please replace "$R^1$" with "R'".

Claim 1: Column 47, line 40, please replace "$R^1$" with "R'".

Claim 1: Column 47, line 43, please replace "$R^1$" with "R'".

Claim 2: Column 48, line 19, please replace "$R^1$" with "R'".

Claim 2: Column 48, line 22, please replace "$R^1$" with "R'".

Claim 5: Column 48, line 52, please replace "$R^1$" with "R'".

Claim 7: Column 49, line 26, please replace "$C_{2-8}$, alkoxy" with "$C_{2-8}$ alkoxy".

Claim 8: Column 49, line 63, please replace "hydroen" with "hydrogen".

Claim 10: Column 50, line 22, please replace "$R^1$" with "R'".

Claim 10: Column 50, line 25, please replace "$R^1$" with "R'".

Claim 10: Column 50, line 27, please replace "$R^1$" with "R'".

Claim 10: Column 50, line 37, please replace "$C^{1-5}$" with "$C_{1-5}$".

Claim 12: Column 50, line 61, please replace "aralky" with "aralkyl".

Signed and Sealed this

Twenty-ninth Day of September, 2009

David J. Kappos
*Director of the United States Patent and Trademark Office*